(12) United States Patent
Hodko et al.

(10) Patent No.: US 7,686,934 B2
(45) Date of Patent: Mar. 30, 2010

(54) THREE DIMENSIONAL DIELECTROPHORETIC SEPARATOR AND METHODS OF USE

(75) Inventors: Dalibor Hodko, Poway, CA (US); Ying Huang, San Diego, CA (US); Daniel D. Smolko, Jamul, CA (US)

(73) Assignee: Gamida for Life B.V., Rotterdam (NL)

( * ) Notice: Subject to any disclaimer, the term of this patent is extended or adjusted under 35 U.S.C. 154(b) by 580 days.

(21) Appl. No.: 11/638,093

(22) Filed: Dec. 12, 2006

(65) Prior Publication Data

US 2007/0187248 A1    Aug. 16, 2007

Related U.S. Application Data

(60) Provisional application No. 60/749,760, filed on Dec. 13, 2005.

(51) Int. Cl.
  *G01N 27/447*  (2006.01)
  *G01N 27/453*  (2006.01)

(52) U.S. Cl. ................................ 204/547; 204/643

(58) Field of Classification Search ............. 204/547, 204/643, 450, 600
See application file for complete search history.

(56) References Cited

U.S. PATENT DOCUMENTS 5,626,734 A * 5/1997 Docoslis et al. ............. 204/547
6,780,584 B1 * 8/2004 Edman et al. .................. 435/6

* cited by examiner

*Primary Examiner*—Alex Noguerola
(74) *Attorney, Agent, or Firm*—John P. White; Cooper & Dunham LLP

(57) ABSTRACT

Devices and methods for performing separation of cell particles by dielectrophoresis in three dimensions. In one embodiment the device comprises a flow chamber having microfabricated chip with a plurality of vertical and horizontal electrodes, which may be coated with a protective layer to prevent direct contact between any electrode and a sample. The horizontal electrodes are in electrical communication with a DC or an AC power source, while the vertical electrodes are in electrical communication with an AC power source.

11 Claims, 27 Drawing Sheets

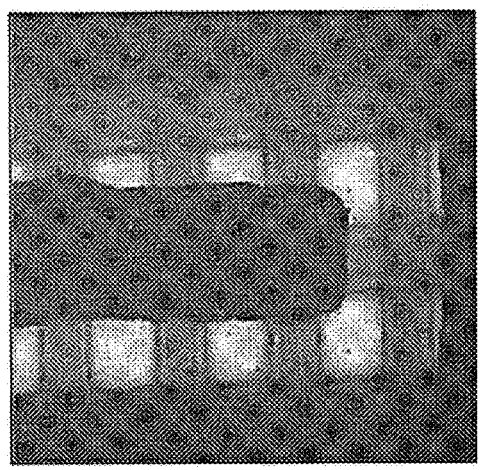 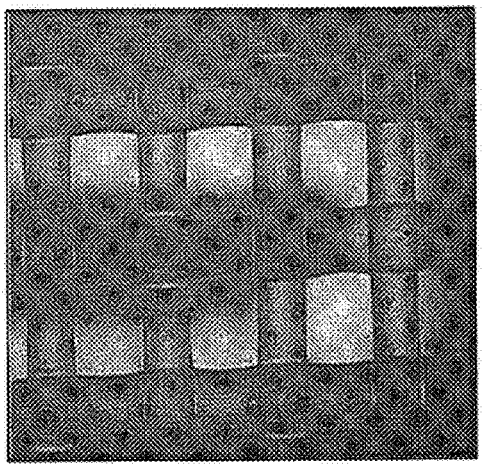
Figure 14A    Figure 14B
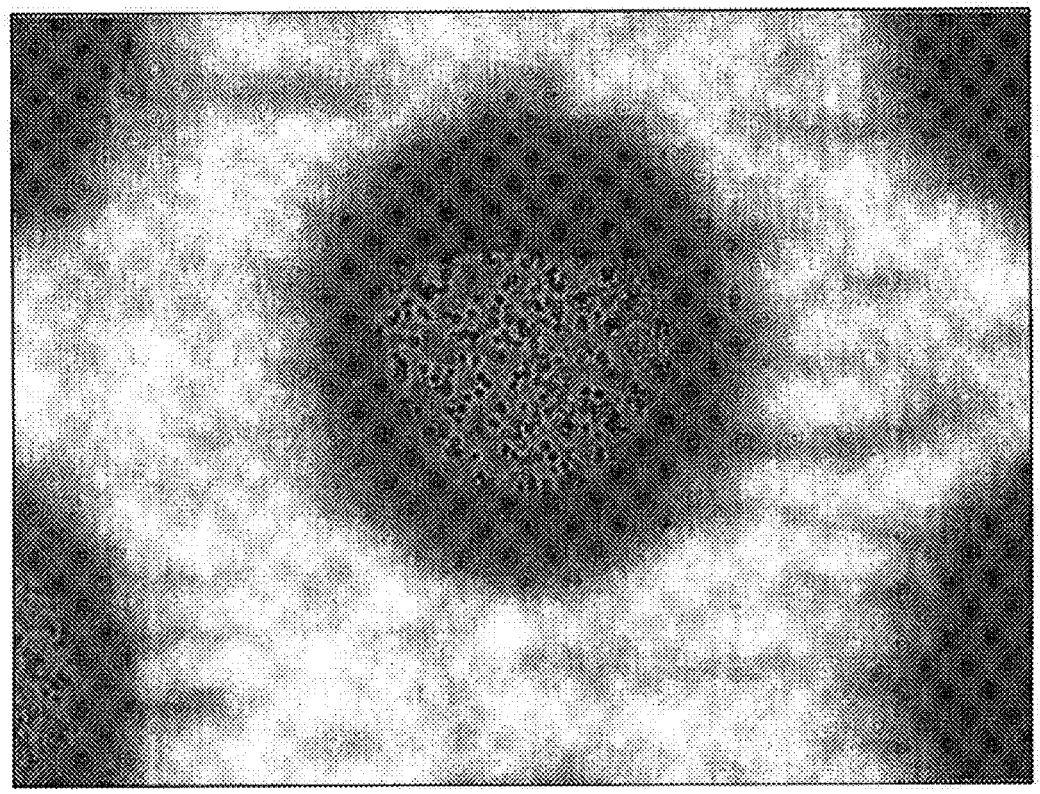
Figure 14C

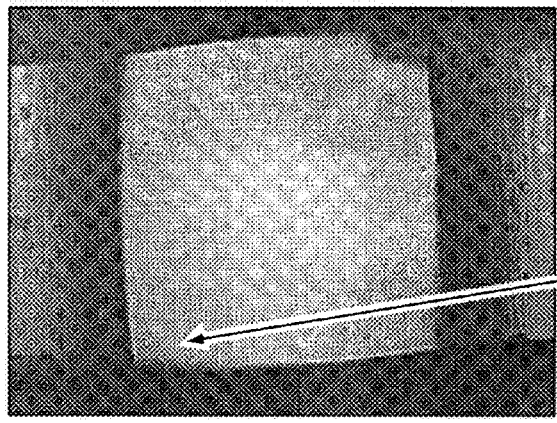 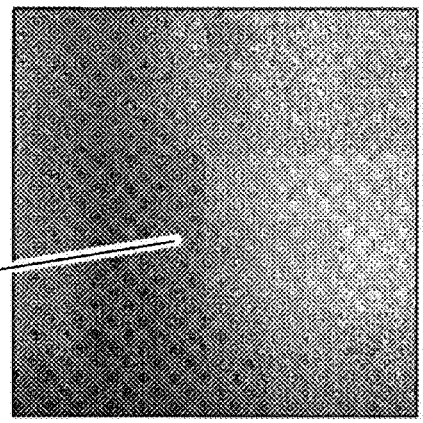
*Figure 16C*  *Figure 16D*
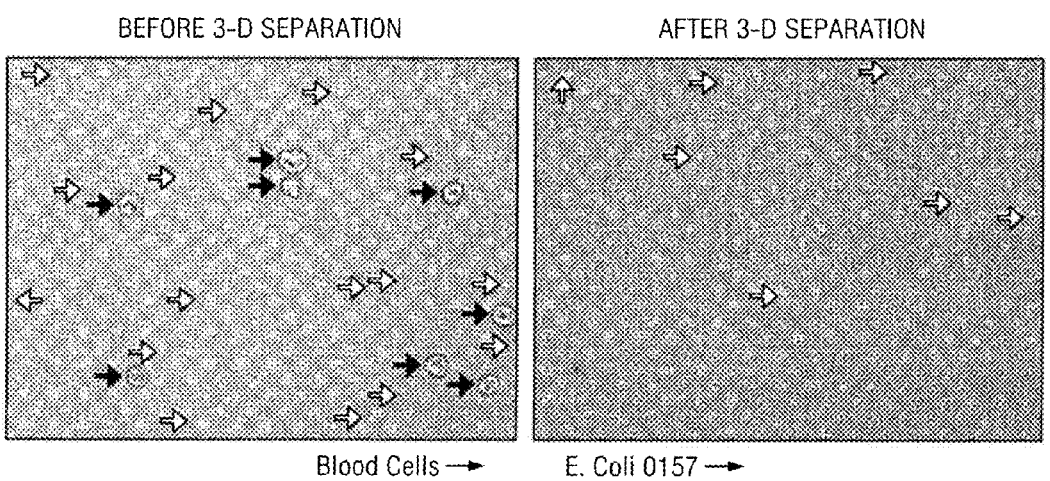
*Figure 17A*  *Figure 17B*

THREE DIMENSIONAL DIELECTROPHORETIC SEPARATOR AND METHODS OF USE

CROSS REFERENCE TO RELATED APPLICATIONS

This patent application claims priority to U.S. patent application Ser. No. 60/749,760, filed Dec. 13, 2005, the specification of which is incorporated herein by reference in its entirety.

FEDERAL FUNDS STATEMENT

This invention was reduced to practice with funds from NIH Project R43 AI 54003-01. The Government may have certain rights to this invention.

FIELD OF THE INVENTION

This invention relates to devices and methods for performing active, molecular and biological sample preparation and diagnostic analyses. It relates generally to devices and methods for electronic cell separation; and more specifically, to devices and methods for achieving three dimensional separation of cells or other bioparticles from biological samples using dielectrophoresis, which can be conducted on a single bioelectronic chip (e.g. in an integrated assay system). These manipulations are useful in a variety of applications, including, for example, food and/or water quality monitoring, infectious disease diagnostics, diagnostics of cancers, bone marrow processing (e.g. stem cell separation and analysis) and genetics-based identification of individuals for forensics purposes.

BACKGROUND OF THE INVENTION

The basis for many molecular-biological and immuno assays, diagnostic assays and tests, among other things, include the steps of obtaining a cellular sample (e.g., blood, tissue, etc.), separating out the cellular material of interest, disrupting or lysing the cells of interest to release the crude DNA and RNA (for simplicity, a reference to DNA in the following text also refers to RNA where appropriate) all protein, purifying the crude lysate (i.e. removing cellular debris), and performing some enzymatic reaction to analyze the lysate as desired.

Dielectrophoresis has become a popular technique for separating microparticles which are either charged or uncharged in solution. Techniques reported prior to this invention are almost always performed in a glass slide based device having exposed (i.e. naked) interdigitated electrodes plated on the surface of the slide and having a flow chamber with a volume of several hundred microliters. Cells are separated in such devices based on their dielectric properties by choosing separation buffer(s) with appropriate conductivity and an AC signal with a suitable amplitude and frequency. These prior devices have several problems, including the following. A first problem is that both separated and unseparated cells bind nonspecifically to the exposed glass surface of the slide and to the exposed electrode surfaces. A second problem is that the volume of the flow chamber (several hundred microliters) is so large that thermal convection disturbs and pushes off cells initially retained by the electrodes. A third problem is that washing off any undesired cells is not easily accomplished without disturbing the cells that are desirably retained on the electrodes, as the desired cells and electrodes stand in the way of fluidic flow and, hence, block the wash flow containing any undesired cells.

Disrupting or lysing cells releases the crude DNA and RNA material along with other cellular constituents. Electronic cell lysing techniques reported prior to this invention are conventionally performed by applying a series of high voltage DC pulses in a macrodevice, as opposed to a microchip-based device. These conventional electronic lysis techniques have several problems, including the following. A first problem is that the electronic lysis conditions specified by commercial macro-device do not release DNA molecules of high molecular weight (larger than 20 Kb) because the high molecular weight DNA molecules do not fit through the pores created in the cell membrane by the prior lysing methods. A second problem is that some nucleic acids originally released in the lysis chamber are lost due to their non-specific binding to the surface of the lysis chamber. A third problem is that the conventional electronic lysis macrodevice works as a stand alone unit such that both dielectrophoretic cell separation and electronic lysis cannot be performed on the same module.

The crude lysate is then purified (i.e., undesired cellular debris is washed off or separated), and then the purified lysate is subjected to enzymatic reaction(s) to prepare the lysate for hybridization, detection, and analysis. Such reactions may include, for example, denaturing, cleaving, or amplifying the lysate. Only after these sample preparation and DNA processing steps, the actual hybridization reaction is performed, and, finally, detection and data reduction convert the hybridization event into an analytical result. These conventional preparation and processing techniques have several problems, including the following. A first problem is that the steps of sample preparation and processing are typically performed separately and apart from the other main steps of hybridization, detection and analysis. In addition, most of these techniques involve carrying out numerous operations (e.g., pipetting, centrifugations, electrophoresis) on a large number of samples. They are often complex and time consuming, and generally require a high degree of skill. Many a technique is limited in its application by a lack of sensitivity, specificity, or reproducibility. For example, these problems have limited many diagnostic applications of nucleic acid hybridization analysis.

Attempts have been made to use dielectrophoresis to separate and identify cells. For example, U.S. Pat. No. 4,326,934 to Herbert discloses a method and apparatus for cell classification by continuous dielectrophoresis. Cells were separated by making use of both the positive and negative dielectrophoretic movement of cell particles. Separated cells were allowed to be characterized and/or classified by viewing the characteristic deflection distance of cells moving through the two electrodes.

Also, U.S. Pat. No. 5,344,535 to Walter et al. discloses a method and apparatus for the characterization of micro-organisms and other particles by dielectrophoresis. Cells were characterized by matching their signature dielectrophoretic collection rates.

And U.S. Pat. No. 5,569,367 to Walter et al. discloses a method and apparatus for separating a mixture using a pair of interdigitated electrodes. The apparatus used two energized interdigitated electrodes that obstruct straight through flow of cells and further separate different types of cells into fractions by applying a non-uniform alternating field. The electrode structure is comprised of interleaved grid-like structures aligned to obstruct flow through the structure.

As exemplified above, several methods of separating cells by dielectrophoresis have been developed. In dielectrophoresis migration, dielectrophoretic forces are applied to drive the migration of different types of cells within the biological sample to different regions of the microelectrode structure. In dielectrophoresis retention, competition between dielectrophoretic forces and fluid-flow forces is exploited to selectively trap cells of interest from a biological sample at electrodes and hold those cells against an imposed fluid-flow stream. Although dielectrophoresis retention has been successfully demonstrated for isolating cancer cells, bacteria, or CD34+ stem cells from blood, two practical deficiencies minimize the effectiveness of this technique in biomedical applications. First, conventional dielectrophoretic systems often consist of a thin, low volume flow chamber utilizing a two-dimensional array of microelectrodes disposed at the bottom of the flow chamber. However, with increasing distance (e.g., more than 10 µm) from the electrode plan, the electric field decays rapidly and the non-uniformity of the field distribution becomes smaller. The dielectrophoretic forces in such two-dimensional systems are only able to collect the cells of interest that are located close to the electrode plane, while cells floating well above the electrode plane can be lost during washing. Second, the dielectrophoretic forces acting on the cells are not the uniform due to the heterogeneous properties among different cells types. Therefore, cells that experience smaller dielectrophoretic properties may be lost during washing steps because the dielectrophoretic forces are not strong enough to hold the cells against the fluid-flow forces.

In addition, attempts have been made to combine certain processing steps or substeps together. For example, various microrobotic systems have been proposed for preparing arrays of DNA probes on a support material. For example, Beattie et al., in The 1992 San Diego Conference: Genetic Recognition, November, 1992, used a microrobotic system to deposit micro-droplets containing specific DNA sequences into individual microfabricated sample wells on a glass substrate. Various attempts have been made to describe integrated systems formed on a single chip or substrate, wherein multiple steps of an overall sample preparation and diagnostic system would be included. For example, A. Manz et al., in "Miniaturized Total Chemical Analysis System: A Novel Concept For Chemical Sensing", Sensors And Actuators, B1(1990), pp. 244-248, describe a 'total chemical analysis system' (TAS) which comprises a modular construction of a miniaturized TAS. Sampling, sample transport, any necessary chemical reactions, chromatographic separations as well as detection were to be automatically carried out. Yet another proposed integrated system is Stapleton, U.S. Pat. No. 5,451,500, which describes a system for automated detection of target nucleic acid sequences in which multiple biological samples are individually incorporated into matrices containing carriers in a two-dimensional format. Different types of carriers are described for different kinds of diagnostic tests or test panels.

Various multiple electrode systems are disclosed which purport to perform multiple aspects of biological sample preparation or analysis. Pace, U.S. Pat. No. 4,908,112, entitled "Silicon Semiconductor Wafer for Analyzing Micronic Biological Samples" describes an analytical separation device in which a capillary-sized conduit is formed by a channel in a semiconductor device, wherein electrodes are positioned in the channel to activate motion of liquids through the conduit. Pace states that the dimension transverse to the conduit is less than 100 µm. Pace also states that all functions of an analytical instrument may be integrated within a single silicon wafer: sample injection, reagent introduction, purification, detection, signal conditioning circuitry, logic and on-board intelligence. Soane et al., in U.S. Pat. No. 5,126,022, entitled "Method and Device for Moving Molecules by the Application of a Plurality of Electrical Fields", describes a system by which materials are moved through trenches by application of electric potentials to electrodes in which selected components may be guided to various trenches filled with antigen-antibodies reactive with given charged particles being moved in the medium or moved into contact with complementary components, dyes, fluorescent tags, radiolabels, enzyme-specific tags or other types of chemicals for any number of purposes such as various transformations which are either physical or chemical in nature. It is said that bacterial or mammalian cells; or viruses may be sorted by complicated trench networks by application of potentials to electrodes where movement through the trench network of the cells or viruses by application of the fields is based upon the size, charge or shape of the particular material being moved. Clark, U.S. Pat. No. 5,194,133, entitled "Sensor Devices", discloses a sensor device for the analysis of a sample fluid which includes a substrate in a surface of which is formed an elongate micro-machined channel containing a material, such as starch, agarose, alginate, carrageenan or polyacrylamide polymer gel, for causing separation of the sample fluid as the fluid passes along the channel. The biological material may comprise, for example, a binding protein, an antibody, a lectin, an enzyme, a sequence of enzymes, or a lipid.

Various devices for eluting DNA from various surfaces are known. Shukla U.S. Pat. No. 5,340,449, entitled "Apparatus for Electroelution" describes a system and method for the elution of macromolecules such as proteins, DNA and RNA from solid phase matrix materials such as polyacrylamide, agarose and membranes such as PVDF in an electric field. Materials are eluted from the solid phase into a volume defined in part by molecular weight cut-off membranes. Okano, U.S. Pat. No. 5,434,049, entitled "Separation of Polynucleotides Using Supports Having a Plurality of Electrode-Containing Cells" discloses a method for detecting a plurality of target polynucleotides in a sample, the method including the step of applying a potential to individual chambers so as to serve as electrodes to elute captured target polynucleotides, the eluted material is then available for collection.

Generally, the prior art processes have been extremely labor and time intensive. Multiple steps requiring human intervention either during the process or between processes are suboptimal in that there is a possibility of contamination and operator error. Further, the use of multiple machines or complicated robotic systems for performing the individual processes is often prohibitive except for the largest laboratories, both in terms of the expense and physical space requirements.

As is apparent from the preceding discussion, numerous attempts have been made to provide effective techniques to conduct sample separation and preparation reactions. However, for the reasons stated above, these techniques are limited and lacking. These various approaches are not easily combined to form a system which can carry out a complete DNA diagnostic assay. Despite the long-recognized need for such a system, no satisfactory solution has been proposed previously.

There is a continuing need for methods and devices which lead to improved dielectrophoretic separation of biological cells as well as improved biological stability of the separated cells. There is also a continuing need for methods and devices which improve cell preparation and analysis, and which are capable of integrating cell separation, preparation, and analysis in a single system.

SUMMARY OF THE INVENTION

This invention broadly relates to devices and methods for performing electronic molecular biological sample separation. It relates, more specifically, to devices and methods for achieving separation of desired cells and undesired cells from a biological sample by three-dimensional dielectrophoresis. The separation can be conducted on a single bioelectronic chip.

In one aspect of this invention, a device comprises a flow chamber having microfabricated chip with a plurality of vertical and horizontal electrodes. The electrodes may be coated with a protective layer which prevents direct contact between any electrode and a sample. The horizontal electrodes are typically in electrical communication with a DC power source, while the vertical electrodes are in electrical communication with an AC power source. In some embodiments, the horizontal electrodes are in electrical communication with an AC power source. The flow chamber comprises an upper chamber and an lower chamber. The upper chamber and lower chamber are separated by a separator having a plurality of openings. The openings may take a variety of shapes and sizes for effecting size exclusion of the biological sample of interest. Representative geometrical openings include circles, squares, triangles, rectangles, parallelograms, rhombus, trapezoids, ellipses, polygons, and combinations thereof.

The flow chamber also comprises an in-port and an out-port which may be further attached to plastic tubing to enable input and output of materials through the in-port and out-port respectively.

One exemplary method of using such a device includes preparation of a cell sample for introduction (e.g., suspension in a cell separation buffer) and subsequent dielectrophoresis; introduction of the sample into the flow cell (e.g., via pumping); subjecting the sample to an AC electric field to dielectrophoretically separate the desired cells from the sample; and subjecting the sample to a DC electric field or an AC electric field to move the undesired cells from the lower chamber to the upper chamber.

In another aspect of the invention, a method manipulates biological samples comprising a mixture of desired and undesired cellular materials. The manipulation is carried out in a dielectrophoretic system including a flow chamber, which has an upper chamber, a lower chamber and an array of electrodes, which may take a variety of forms, including horizontal and vertical, to which a combination of AC and DC electric fields may be applied. The method includes introducing a biological sample into the flow chamber of the system and subsequently subjecting the biological sample to a dielectrophoretic force in the lower chamber such that the desired cells collect in the lower chamber and the undesired cells collect in the upper chamber. In other aspects, an AC field amplitude ranging from about 1V to about 48V is applied to the vertically arranged electrodes in the flow chamber, while a DC frequency ranging from between about 1 Hz to about 150 kHz is applied to the horizontally arranged electrodes in the flow chamber. In yet another aspects, immunological reagents may be applied to the biological sample before it is introduced into the flow chamber, while in other aspects, the immunological reagents may be added to the flow chamber at or around the same time the biological sample is introduced into the flow chamber.

Therefore, a primary object of the present invention is to provide devices and methods for conducting cell separation.

An additional object of the present invention is to provide devices and methods for conducting cell separation, on a single chip so that mechanical manipulation such as pipetting and centrifugation can be omitted.

A further object of the present invention is to provide devices and methods for providing a combination of electrode addressing, a buffer, and the use of AC and DC currents to accomplish three dimensional, uniform separation of desired cells.

Still a further object of the present invention is to provide devices and methods for providing uniform separation of desired cells with minimized non-specific adhesion of cells to the flow chamber and/or electrodes.

Yet a further object of the present invention is to provide devices and methods for three-dimensional separation of desired cells without the disruption associated with a washing step.

Another object of the present invention is to provide electronic arrays capable of extending dielectrophoretic forces substantially throughout a flow chamber so as to facilitate efficient separation without the need for a washing protocol.

BRIEF DESCRIPTION OF THE DRAWINGS

FIG. 11 shows a time-course of three-dimensional dielectrophoretic separation of polystyrene microparticles using screen printed carbon electrodes. FIG. 11D is 3 minutes.

FIG. 12 shows three-dimensional dielectrophoretic separation of particles at with an AC frequency of 110 kHz.

FIGS. 16A-16D are photographs demonstrating the separation of blood cells in the bottom compartment (16A and 16B) away from bacteria in the upper compartment (16C and 16D).

FIGS. 17A-17B are photographs demonstrating the result of a method for determining efficiency of 3D DEP separation and collection.

DETAILED DESCRIPTION OF THE INVENTION

Figure 1:
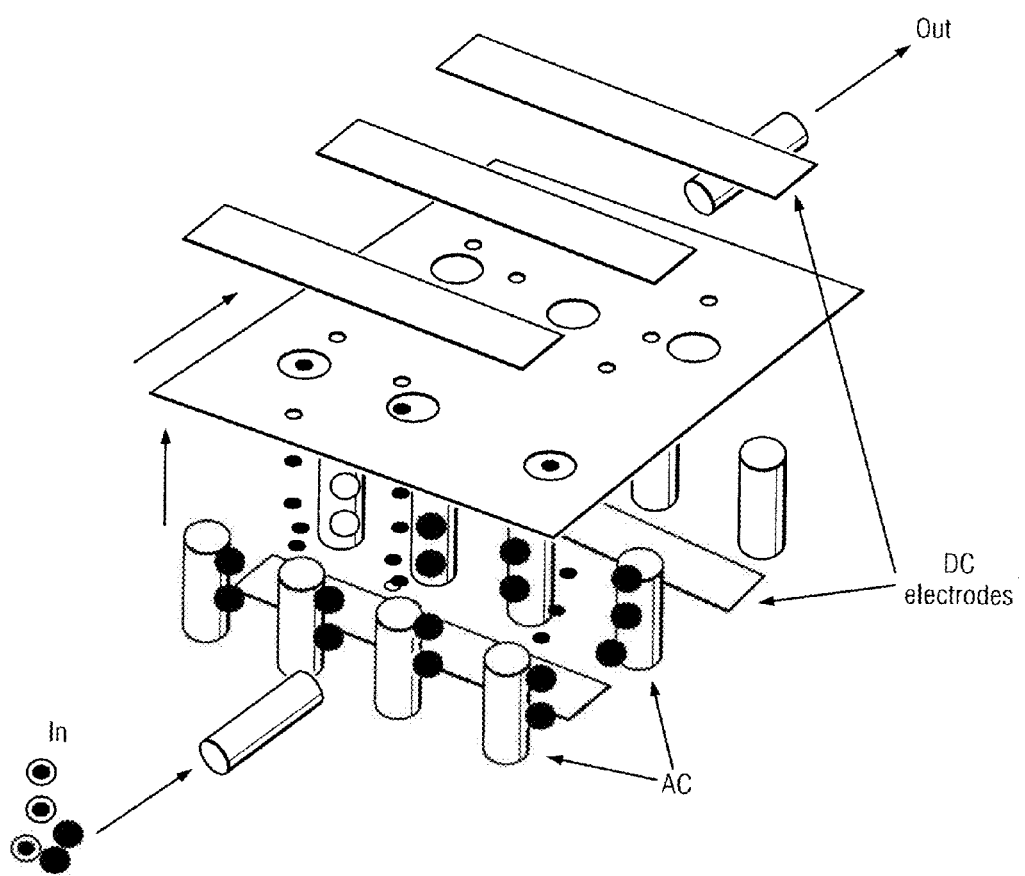
FIG. 1 is a schematic view of the three-dimensional dielectrophoretic apparatus of the present invention, including horizontal and vertical oriented electrodes.
Figure 2A:
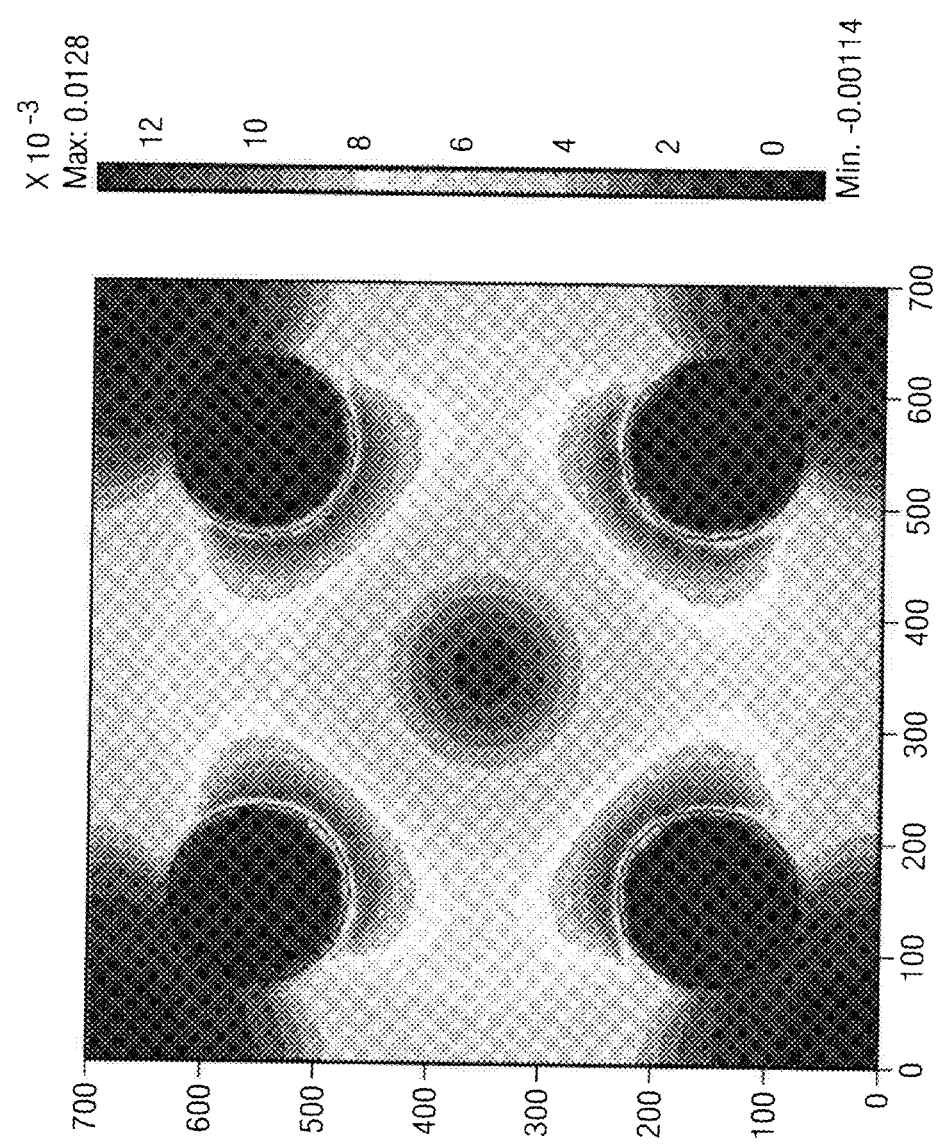
FIG. 2 shows a comparison of fluid dynamics modeling of dielectrophoretic forces in a cylindrical and interdigitated electrode array.
Figure 2B:
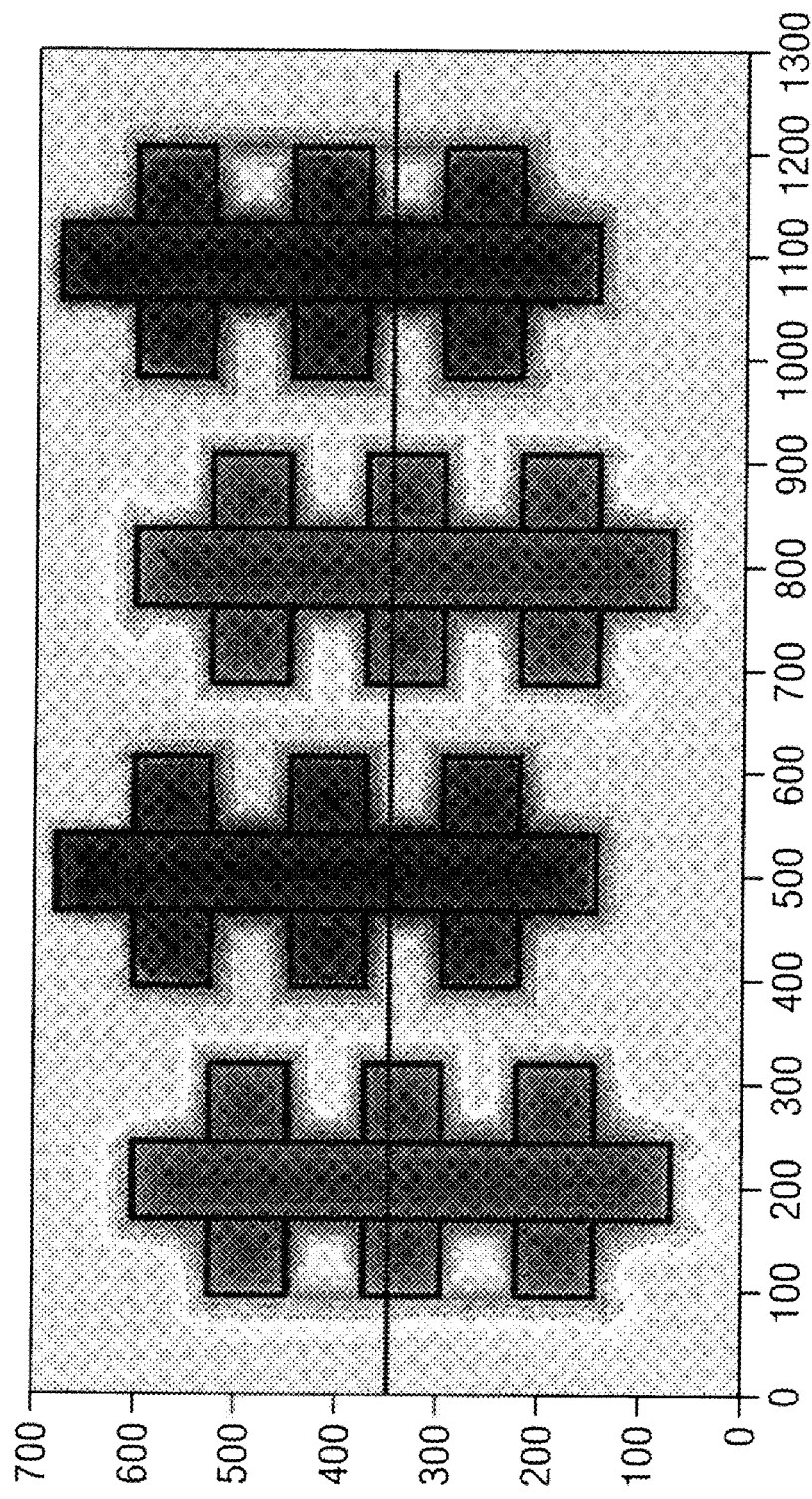

The present invention comprises devices and methods for performing separation of cell particles by three-dimensional dielectrophoresis, which can be conducted on a single bioelectronic chip.

The basic theory of dielectrophoresis, motion of particles with induced polarization under non-uniform electric field, has been extensively studied. See, e.g., R. Pethig, "Dielectrophoresis: Using Inhomogeneous AC Electrical Fields To Separate and Manipulate Cells", Crit. Rev. Biotech, 16:331-48 (1996); X. Wang, et al., "A Unified Theory of Dielectrophoresis and Travelling Wave Dielectrophoresis", J. Phys. D: Appl. Phys., 27:1571-74 (1994); G. Fuhr, "Cell Manipulation and Cultivation Under AC Electric Field Influence in Highly Conductive Culture Media", Biochim. Biophys. Acta 1158: 40-46 (1993); and M. Washizu, "Molecular Dielectrophoresis of Biopolymers", IEEE Trans. Industry Applicat. 30:835-43 (1994). The dielectrophoresis phenomenon can be generally described by energy potential $$\Psi = -m \cdot E$$

where m is the induced dipole moment of a particle suspended in dielectric medium and E is the applied electric field. Therefore, the dielectrophoretic force acting on a particle can be written as a gradient of energy potential.

When the particle has zero net charge and the surrounding medium is isotropic, the average energy potential can be simplified as $$\Psi = -(1/2) p v E^2$$

where p is the effective polarizability of the suspended particle with volume v. The value and sign of polarizability (p) depends on the permittivity of particle and medium, as well as the frequency of the applied electric field. R. Pethig, "Dielectrophoresis: Using Inhomogeneous AC Electrical Fields To Separate And Manipulate Cells", Crit. Rev. Biotech., 16:331-48 (1996). At steady state, the particle with positive polarizability (p>0) will tend to stay at the high-field region and the particle with negative polarizability (p<0) will stay at the low-field region.

To model the distribution of the electric field around the electrodes 24 of the present invention, the following two assumptions were made: First, within the low frequency range the dimensions of both chip and flow chamber are much smaller than the wavelength of the applied AC field. Second, the sample solution has electroneutrality. Under these two assumptions the electric field can be calculated for a particular addressing configuration in the present experiment set-up by solving Laplace's equation $$\nabla^2 \phi = 0 \text{ and } E = -\nabla \phi_-$$

($\phi_-$ is electric potential) with boundary conditions of fixed voltage on electrodes and zero normal current on the rest of the surface, $\phi = V_0$ at positive electrodes, $\phi = 0$ at negative electrodes, and $\delta\phi/\delta n = 0$ at the rest of the chip surface and the flow chamber.

The electric field in the sample solution, and, therefore, the energy potential of polarized particles, is numerically calculated by the finite-difference method. See, K. Binns, "The Analytical and Numerical Solution of Electric and Magnetic Fields" (John Wiley & Sons, N.Y. 1992).

The frequency at which the E. coli cells were subject to the positive dielectrophoretic force and blood cells were subject to the negative dielectrophoretic force was empirically determined by subjecting the cell mixture to different conditions. The investigation was conducted by gradually increasing the frequency of the sinusoidal signal (10 volts peak-to-peak) starting from 5 KHz. When the frequency reached 10 KHz, evident separation of E. coli cells and the rest of the human blood cells was observed. These electrical parameters were later used for the isolation of the E. coli cells.

A preferred embodiment of the present invention comprises a flow chamber, shown in FIG. 1, having an upper chamber and a lower chamber, an inlet and an outlet. The flow chamber preferably has a volume of between about 0.5-5.0 ml. The flow chamber also includes output pins for electronically connecting the flow chamber to an electronic controller (e.g. instrument or computer).

Disposed within the flow chamber is a three-dimensional array of microelectrodes. The three-dimensional array includes vertical microelectrodes and horizontal microelectrodes. The horizontal microelectrodes may have dimensions of between about 50-100 μm in the X-Y plane. The vertical microelectrodes have a height up to about 300 μm.

Figure 3A:
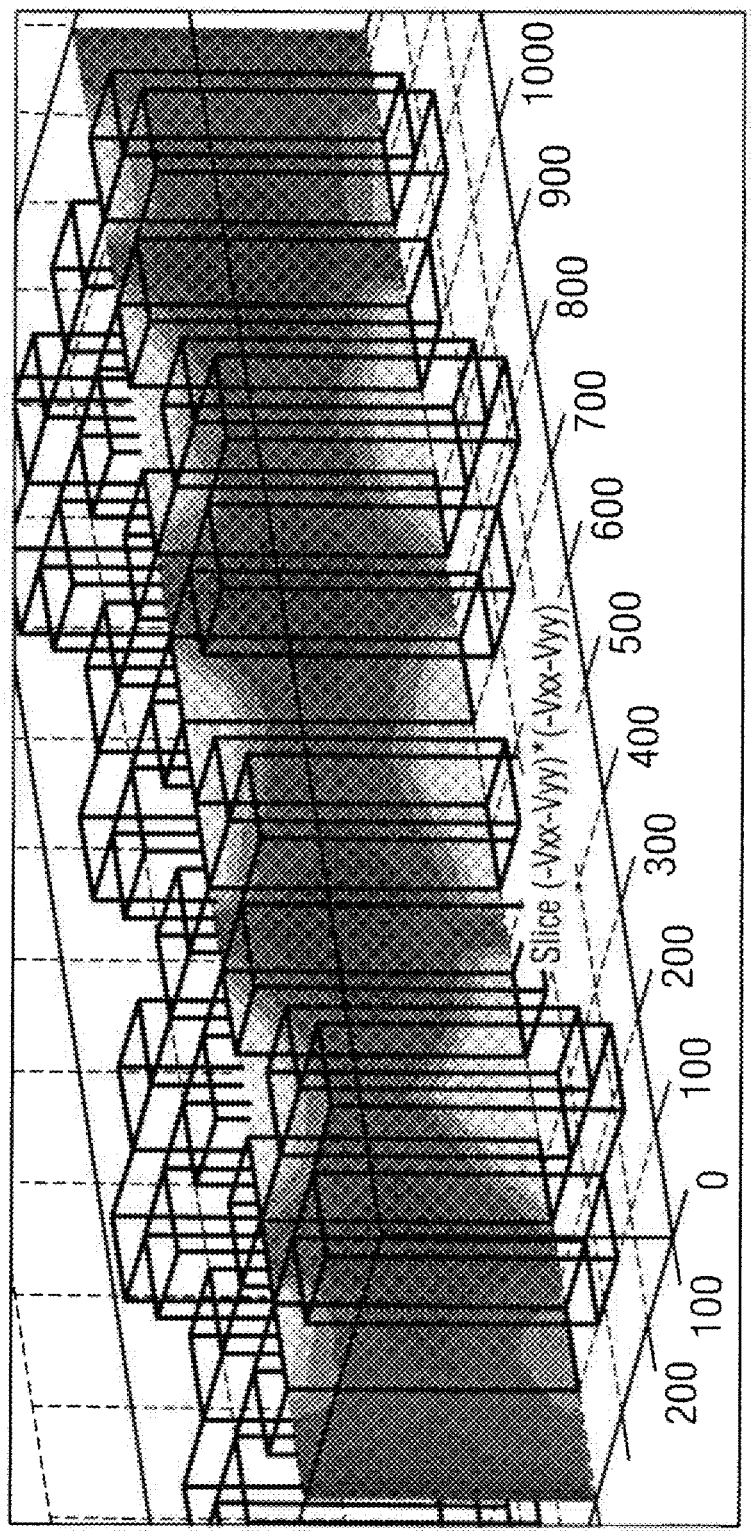
FIG. 3A shows the depth distribution of a dielectrophoretic field in an electrode array wherein the electrodes are of equal heights.
Figure 3B:
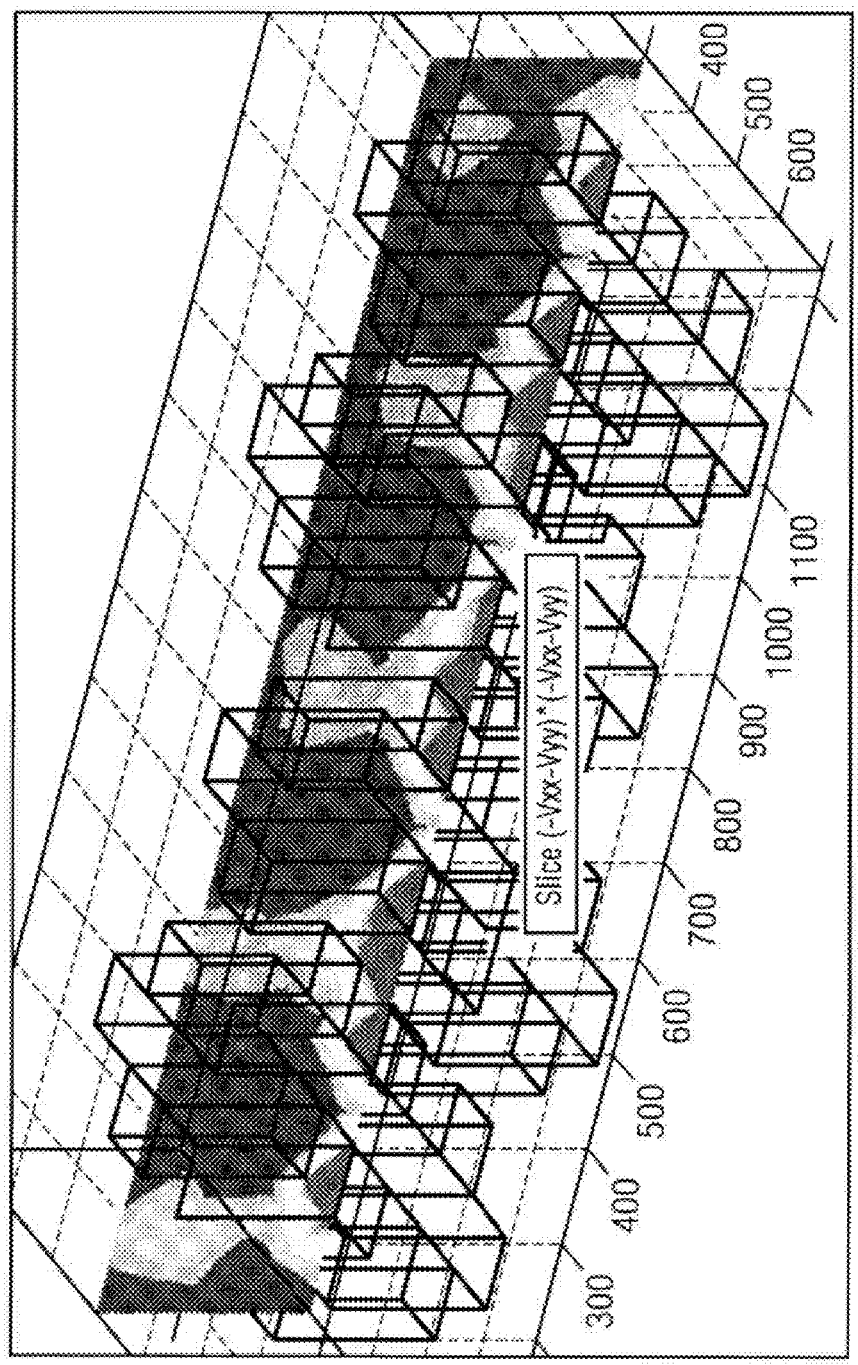
FIG. 3B shows the depth distribution of a dielectrophoretic field in an electrode array wherein the electrodes are of unequal heights.
Figure 4A:
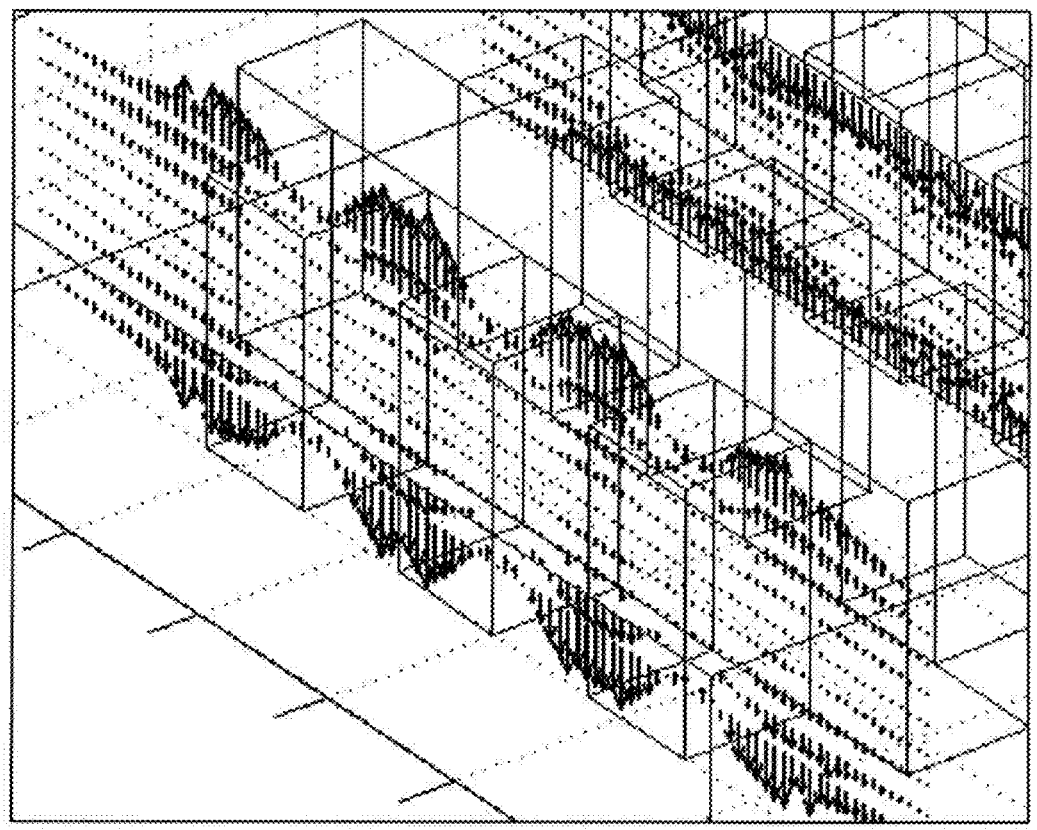
FIG. 4A shows a vectorial plot of dielectrophoretic force distribution in an interdigitated electrode system for various, equal electrode heights.
Figure 4B:
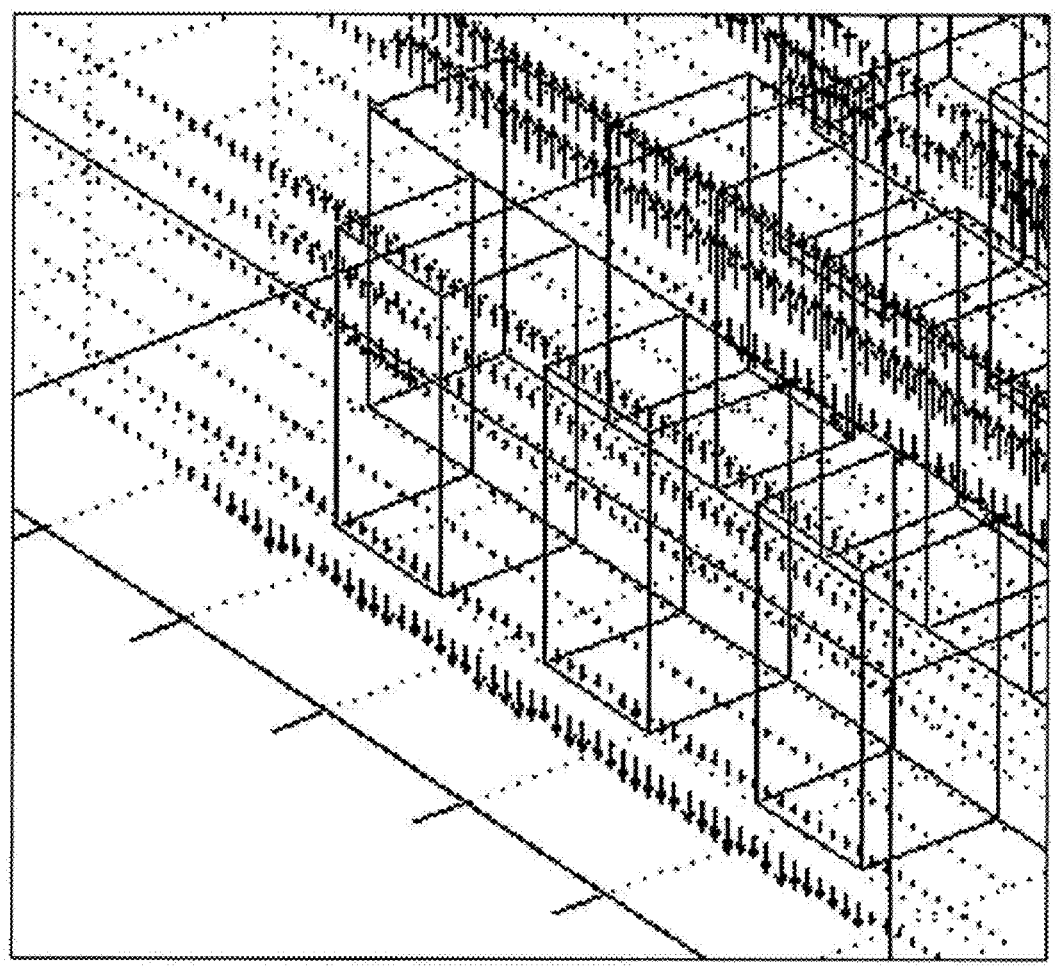
FIG. 4B shows a vectorial plot of dielectrophoretic force distribution in an interdigitated electrode system for various, unequal electrode heights.
Figure 5A:
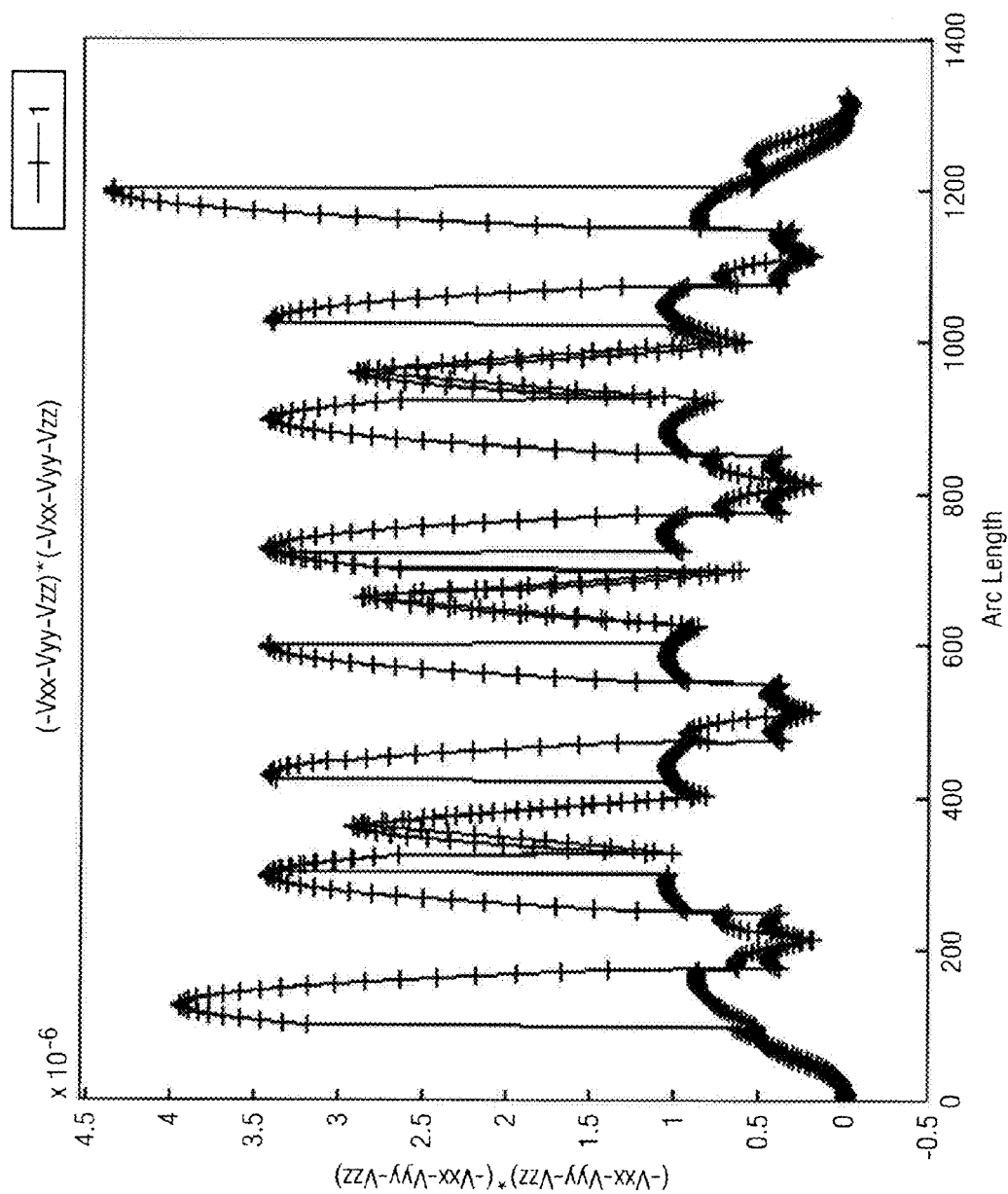
FIGS. 5A and 5B show distribution of dielectrophoretic forces in a three-dimensional (5A) and two-dimensional (5B) systems.
Figure 5B:
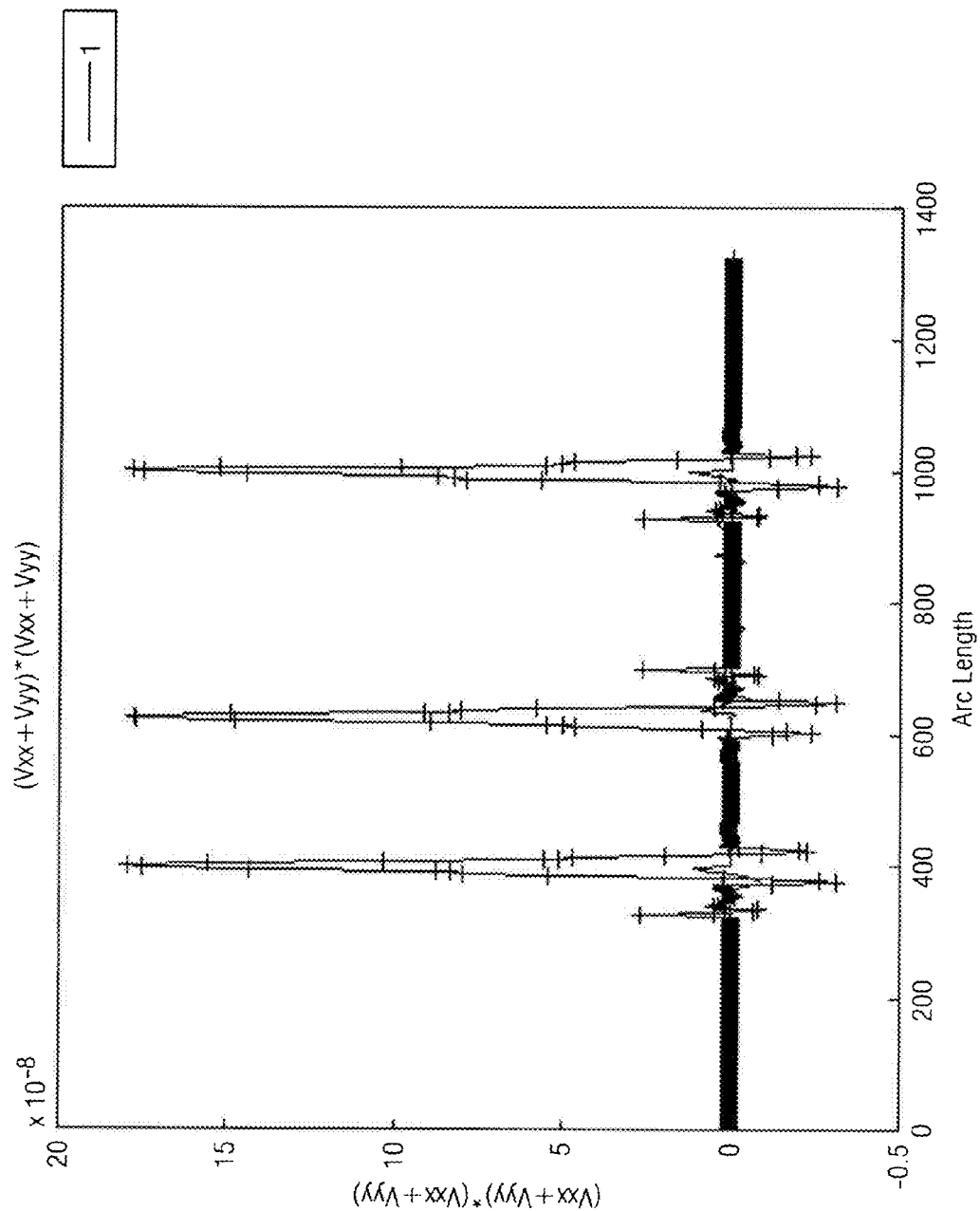

The microelectrodes of the three-dimensional array may be fabricated in cylindrical, interdigitated, straight lines, or other patterns and geometrical shapes. However, an interdigitated pattern is generally more efficient and exhibits higher dielectrophoretic force than a cylindrical pattern. The vertical height of the microelectrodes may be equal or unequal. As shown in FIGS. 3-4, microelectrodes of the same height provided a more well-defined symmetrical regions of high-field and low-field areas. These regions tend to form well-defined electric traps that facilitate particle capture. As shown in FIGS. 5a-5b, the maximum dielectrophoretic forces obtained utilizing the three-dimensional microelectrode array of the current invention were generally about 20 times greater than the maximum dielectrophoretic forces obtained in systems utilizing two-dimensional, interdigitated microelectrode arrays. Moreover, in the three-dimensional microelectrode array of the present invention, the dielectrophoretic forces extend to a depth of about ⅓ the height of the flow chamber, thereby availing the apparatus of the present invention to greater dielectrophoretic forces throughout the area of the flow chamber.

Electrical connections to the microelectrode arrays were made using three-dimensional pin micropositioners. Electric fields were applied using Keithley power sources that monitored both voltage and currents applied.

In some embodiments requiring higher voltages and a broader range of frequencies, a modified DC/AC power supply was developed to provide increased flexibility in choosing the amplitude, waveform and frequency of applied electric signals. Specifically, the power supply used for embodiments requiring superimposed AC/DC fields consisted of three main components. First, a computer control system with two D/A and A/D (National Instruments) having a PCI 6713 card with its own internal D/A waveform generators capable of achieving frequencies of about 1 MHz and a PCI MIO-16E-4 voltage/temperature measurement board. Second, the computer control system includes a Labview program interface that was specifically written to make use of the capabilities of both PCI cards and to address the six D/A outputs on the PCI 6713 card and the six inputs on the PCI MIO-16E-4 to take process measurements. The waveform card can generate standard and any programmed waveform between 0 and ±10V in amplitude and from DC to 1 MHz in frequency. The standard waveforms include DC, Sine, Cosine, Square, Ramp and Triangular waveforms. Third, a Labview software control script was incorporated into the software to allow the user to run programs that either change in time or are based on process inputs.

A multi-functional push-pull amplifier receives the output from the cards. The output from the amplifier, depending on the input, can range from 0 to 10V in/0 to 10V out and from 1 to 10V in/0 to 10,000V output. The amplification factor depends on the selected channel. All the amplifier outputs are all floating except the first. The floating outputs enable to user to bias voltages relative to other outputs without shorting any of the outputs to ground. The floating outputs are biased relative to one another as is the case when a DC electrophoresis (amplitude up to −3.75V) was superimposed with AC dielectrophoresis (e.g., at 90 kHz and 28V without concern for shorting any outputs to ground). Outputs from the amplifier were routed through 40 kV cables.

Immunological Reaction Components

As used herein, "immunoreaction" or "immunological reaction" generally refers to a specific binding reaction between an antibody, or antibody-like molecule, and an antigen, or an epitope-bearing molecule, in addition to further specific binding interactions utilized to detect the antigen-antibody immunoreaction complex. In general, the immunological reactions can be described in terms of three types of components: binding or capture components, analyte components (which may include, for example, an entire bacterial cell, or merely a protein toxin antigen from a lysed cell), and detection or labeling components. These are the basic components of most immobilized immunoassay formats, including traditional sandwich and competitive binding assay formats. In the case of sandwich formats, the immunoreaction complex may include one or more layers of labeling components in order to generate a signal to detect the presence of the analyte in the sample. In the case of competitive immunoassay formats, a known amount of the analyte itself is labeled, and the extent of the binding of this labeled analyte in the presence, and absence, of the sample is determined. Any of the traditional immunoassay formats, including sandwich and open-sandwich formats, competitive binding formats, and others, may be utilized in the present invention.

For the purposes of this invention, an "antigen" is a molecule which presents an immunochemically reactive entity which presents antigenic determinants which comprise a particular spatial arrangement of atoms which is recognizable by an antibody, or an "epitope." Antigenic molecules which induce an immune response are usually quite large. Many antigens are proteins, polypeptides, polysaccharides, proteoglycans, glycoproteins, lipopolysaccharides, and other biologically derived macromolecules (which may be subcellular constituents). Bioparticles such as cells, bacteria, or virus, and also larger subcellular constituents such as cell surface membranes, cell surface proteins, cell surface receptor and effector sites, organelles, nuclei, mitochondria, ribosomes, synthetic micelles, and other natural or synthetic surfaces also present epitopes which can be recognized by antibodies, usually in the form of a molecular portion of the overall structure. However, the epitope recognized by an antibody is usually a small structure, and only a portion of the whole antigen. Thus, the molecules of "antigens" also comprise smaller portions of a naturally occurring antigen which contain an epitope (e.g., periodate digested bacterial polysaccharides), as well as synthetic molecules (peptides, polysaccharides, etc.) which have been designed to mimic an epitope. For convenience, these molecules will be referred to throughout as "antigens," although this usage of the term understood to encompass all of the epitope-bearing molecules described above.

As referred to herein, an "antibody" is a structure that has specific affinity for an epitope. These include any multiple polypeptide chain-containing molecular structure that has a specific shape which fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal "antibody" molecule is the antibody, and all types of immunoglobulins (IgG, IgM, IgA, IgE, IgD), immunoglobulin fragments comprising the binding site (i.e., Fab', papain, pepsin, or ficin fragments), derivatized immunoglobulins (with added chemical linkers, detectable moieties [fluorescent dyes, enzymes, substrates, chemiluminescent moieties], specific binding moieties [such as streptavidin, avidin, or biotin], etc.), recombinant immunoglobulins, single-stranded engineered immunoglobulins and humanized or hybrid immunoglobulins. "Antibodies" also may include artificial antibody-like molecules, such as the triad-peptide "finger" constructs described in WO 01/13126, entitled "Microelectronic Molecular Descriptor Array Devices, Methods, Procedures, and Formats for Combinatorial Selection of Intermolecular Ligand Binding Structures for Drug Screening," or analogs thereof. For convenience, the term "antibody" will be used throughout to generally refer to these molecules, although the term will encompass all immunoglobulins, derivatives, fragments, and modifications as described above.

As referred to herein, "immunoreagents" are molecules comprising an antibody, as defined. Capture immunoreagents generally comprise moieties for attachment to the permeation layer of an active electronic matrix device. These may include, for example, moieties for non-covalent attachment, such as biotin, streptavidin, avidin, other biotin binding proteins, phenyl boronic acid (PBA), salicylhydroxamic acid (SHA), or synthetic binding systems such as those described using pyranosyl RNA or necleo-delta-peptides (CAN) in WO 01/13126.

Immunoreagents may also be detection immunoreagents which have been detectably labeled with one or more moieties for detection. Distinguishably detectable labeling moieties, detectable moieties, or reporter group(s) for use in the inventions are preferably fluorophores. However, also suitable are chromophores, biotin/avidin detection systems (if biotin/avidin is not utilized to immobilize capture Immunoreagents), chemiluminescent agents (such as acridinium), enzymes, gold particles, magnetic beads, metal chelates, radioisotopes, other antibodies, and nanoparticles. Suitable fluorophores include active-ester or other reactive derivatives of BODIPY.sub.630/650 X-SE, Texas Red X-SE, or BODIPY TRX-SE, Cy-dyes, fluorescein, rhodamine, phycoerythrin, Lissamine, and coumarin, and Alexa dyes.

In order to electrophoretically transport toxin proteins and immunoreagents for immunochemical reactions, the isoelectric points of these proteins should be known and the pH of the addressing conditions adjusted, if necessary, to determine the direction that each protein (or other sub-cellular constituent) on the device will travel in the applied electric field. Isoelectric points may be measured using a variety of techniques well known in the biochemical arts. From the isoelectric point, the polarity of the reagents at pH 7.5 in 50 mM histidine (a buffer of choice for electrophoretic transport on active electronic matrix devices) may be deduced. Although 50 mM histidine is the buffer of choice, other low-conductivity buffers at other pHs may be used when necessary to ensure that the immunoreagent or sub-cellular constituent will migrate towards the biased electrode. In the examples, buffers and pHs have been chosen so that the immunoreagents and toxins are negatively charged, and migrate towards a positively biased electrode in an applied DC field. However, persons of skill in the electrophoretic arts may easily modify the described addressing conditions to accommodate proteins or other sub-cellular constituents which are positively charged.

As will be appreciated by those of skill in the art, the placement of capture immunoreagents on the electrode array will depend on the format of the assay in which the device will be used. For instance, where the desired bioparticles (e.g., bacterial cells, spores, or viruses) are to be collected in high-field regions, the capture immunoreagents would be immobilized at the microlocations whose electrodes will be used to generate the AC field. Conversely, if the desired bioparticles are to be collected in low-field areas, the capture immunoreagents would be immobilized at microlocations located within the expected low-field areas between microlocations whose electrodes will be used to generate the AC field. In some embodiments, such capture immunoreagents could be immobilized by mechanical application between microlocations prior to the sealing of the electrode array within a flow cell for later passive immunoreaction labeling (e.g., between the microlocations where a checkerboard biasing pattern is to be used.) However, it is preferred to design the biasing pattern so that microlocations are located in the low-field areas (which could be easily accomplished in a concentric square pattern, for instance), so that the microlocations may be later used to electrophoretically transport detection immunoreagents to the microlocations containing the captured bioparticles.

If proteins, organelles, or other immunologically reactive analytes from lysed bioparticles collected by DEP techniques are to be detected using electrophoretically enhanced immunoassay techniques, as described below, then several options exist for placement of the capture immunoreagents for the assay. The capture immunoreagents may be immobilized at the microlocations where the bioparticles to be lysed are to be gathered, or at other microlocations which may or may not be part of the portion of the array utilized in the DEP separation. For example, in a 10 by 10 array of microlocations where a 5 by 5 corner section is to be utilized for DEP, the capture immunoreagents for the sub-cellular analyte immunoassay may be immobilized on microlocations in an adjacent section of the array. Or, alternatively, another active electronic matrix device may be used within the same flow cell for this purpose, or within another fluidly connected flow cell. Such arrangements are described in U.S. Pat. Nos. 6,280,590 and 6,071,394, referenced and discussed above.

Bioparticles may be separated to predetermined areas of low or high AC field strength on the active electronic matrix chip devices by applying an AC current through the microlocation electrodes. By utilizing immunoreagents in detection and/or capture roles, the sensitivity, specificity, and usefulness of this technique can be greatly improved.

Some bioparticles have inherent "sticky" properties (e.g., the *B. globigii* spores), and can adhere non-specifically to the permeation layer surface due to their chemical or physical properties. When the electrode array microlocations are biased in a pattern so that areas of expected aggregation of the bioparticles in the AC field are at microlocations of the device, the bioparticles may be collected at "aggregate" microlocations. This is most easily accomplished for bioparticles which migrate to high field strength areas, as these naturally lie on the biased microlocations. However, by careful design of the biasing pattern, aggregate microlocations lying in low field areas may also be provided. After DEP isolation of "sticky" bioparticles, the aggregate microlocations may be used for immunodetection of the bioparticles. By introducing a solution of detection immunoreagent specific for the bioparticle (e.g., a fluorescently labeled polyclonal goat antibody), and biasing the aggregate microlocation electrode to electrophoretically transport the detection immunoreagent to the aggregate microlocation, as described above. After the detection immunoreagent has bound to the bioparticle at the microlocation, and optionally washing unbound immunoreagent from the device, the presence of the bioparticle on the microlocation may be detected by detecting the label on the immunoreagent. Optionally, if a concentration standard curve is established with known concentrations of the bioparticle, the technique can also be used to quantify the amount of immobilized bioparticle at the microlocation. Although the bioparticle on the aggregate microlocation may be detected by non-electrically mediated labeling techniques, such as cell dye stains or passive incubation with the detection immunoreagent according to traditional immunoassay procedures, the methods of the invention provide the advantages of decreased time of assay and increased specificity over the traditional techniques.

In cases where the bioparticle is not inherently "sticky", capture immunoreagents may be utilized to enhance the retention and immobilization of the bioparticles during and after the DEP process. If a capture immunoreagent specific for the bioparticle (e.g., a biotinylated mouse monoclonal antibody specific for *S. auraleus*) is immobilized at the aggregate microlocation, bioparticles aggregating at the microlocation during the DEP process will be specifically and firmly retained at the microlocation. Thus, the isolated bioparticles may retained during more vigorous washes to remove unwanted sample constituents, without maintaining the AC field. The immunoimmobilized bioparticle may then be preferably detected on the aggregate microlocation by an electrophoretically enhanced detection immunoreaction.

Microelectrode Array Fabrication

Prior to actually fabricating the three-dimensional electrode arrays, computer modeling and dielectric characterization studies were conducted. To efficiently design the three-dimensional dielectrophoretic arrays, CoventorWare's computerized fluid dynamics software was used to model designs. The modeling included comparison of two- and three-dimensional forces, design and optimization of three-dimensional array patterns to determine optimal electrode spacing, height and geometric shape.

The computer modeling showed that similar to two-dimensional dielectrophoretic system, three-dimensional arrays having interdigitated electrode patterns were more efficient and exhibited greater dielectrophoretic force than cylindrically shaped electrodes. A comparison of interdigitated electrodes have equal and unequal heights demonstrated that an array of electrodes of the same height provided more well-defined symmetrical regions of high-field and low-field areas, as shown in FIGS. 3 and 4. The symmetrical regions tended to form well-defined electric field traps for capturing particles.

The computer modeling also demonstrated that the maximum DEP forces in a three-dimensional array were generally about 20 times the maximum DEP forces in comparable two-dimensional, interdigitated arrays, as shown in FIGS. 5A and 5B. However, in three-dimensional arrays, these increased forces are maintained to a depth of about ⅓rd of each side of the flow chamber, thereby allowing the DEP forces to act throughout a greater portion of the flow chamber.

Figure 6:
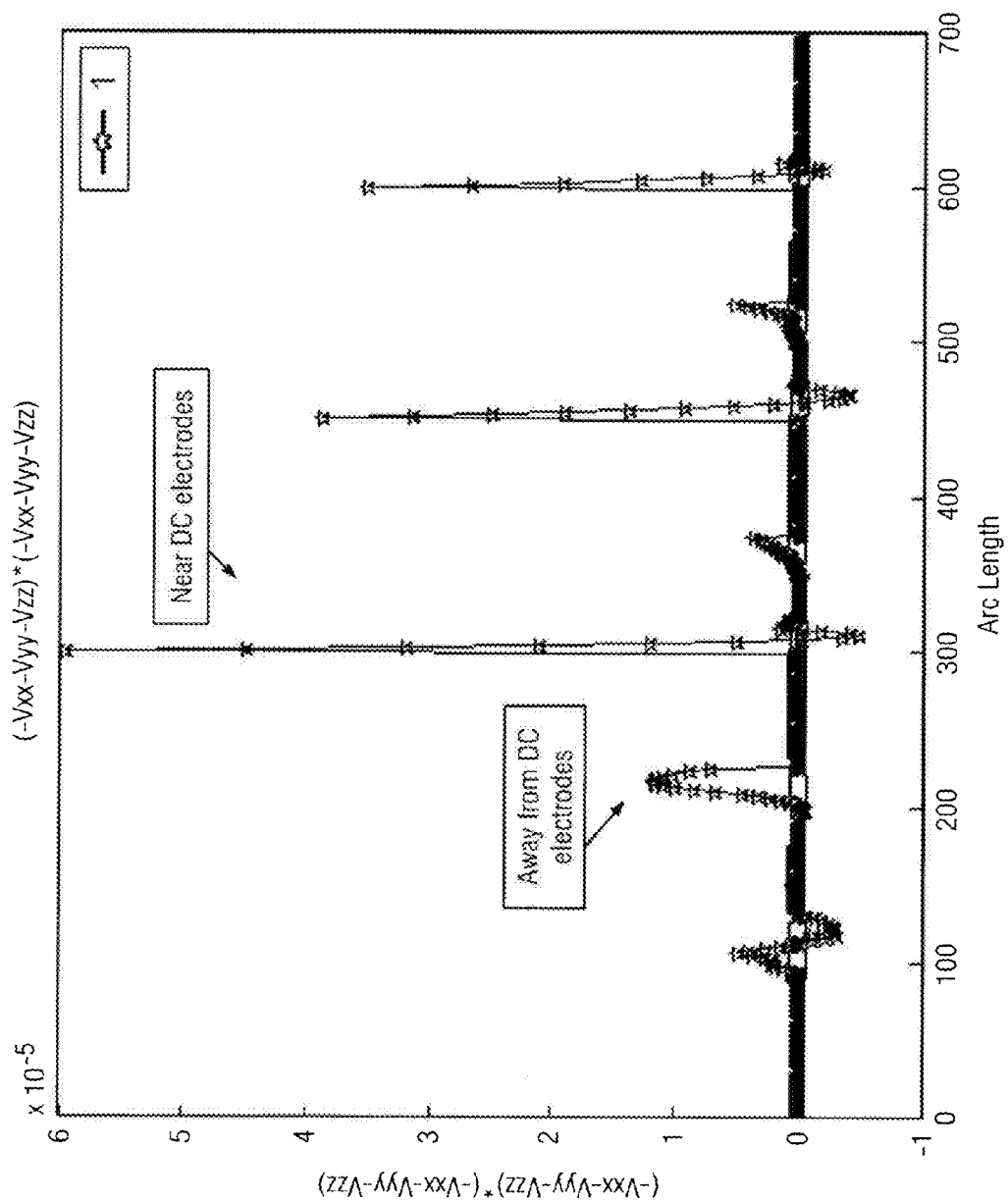
FIG. 6 shows distribution of electric field gradients in the presence of a superimposed DC/AC field near and away from the DC electrodes.

In accordance with another embodiment, computer modeling demonstrated that AC and DC electric fields could be superimposed within the flow chamber by adding DC biasing electrodes. Addition of the DC biasing electrodes effected the relative magnitudes of the dielectrophoretic and electrophoretic fields within the flow chamber, as shown in FIG. 6. Specifically, when both AC and DC biasing currents were present (AC bias RMS=1.0 V; DC bias=1.0/−1.0 V), the dielectrophoretic force in the flow chamber increased by a factor of 100.

The three-dimensional microelectrode arrays were fabricated using four different methods: (i) lithographic etching of laminated printed wiring boards coated with photoresist; (ii) pyrolized conductive carbon photoresist (PCC); (iii) carbon screen-printing; and (iv) sputtering and patterning with an ink-jet printer.

Figure 7:
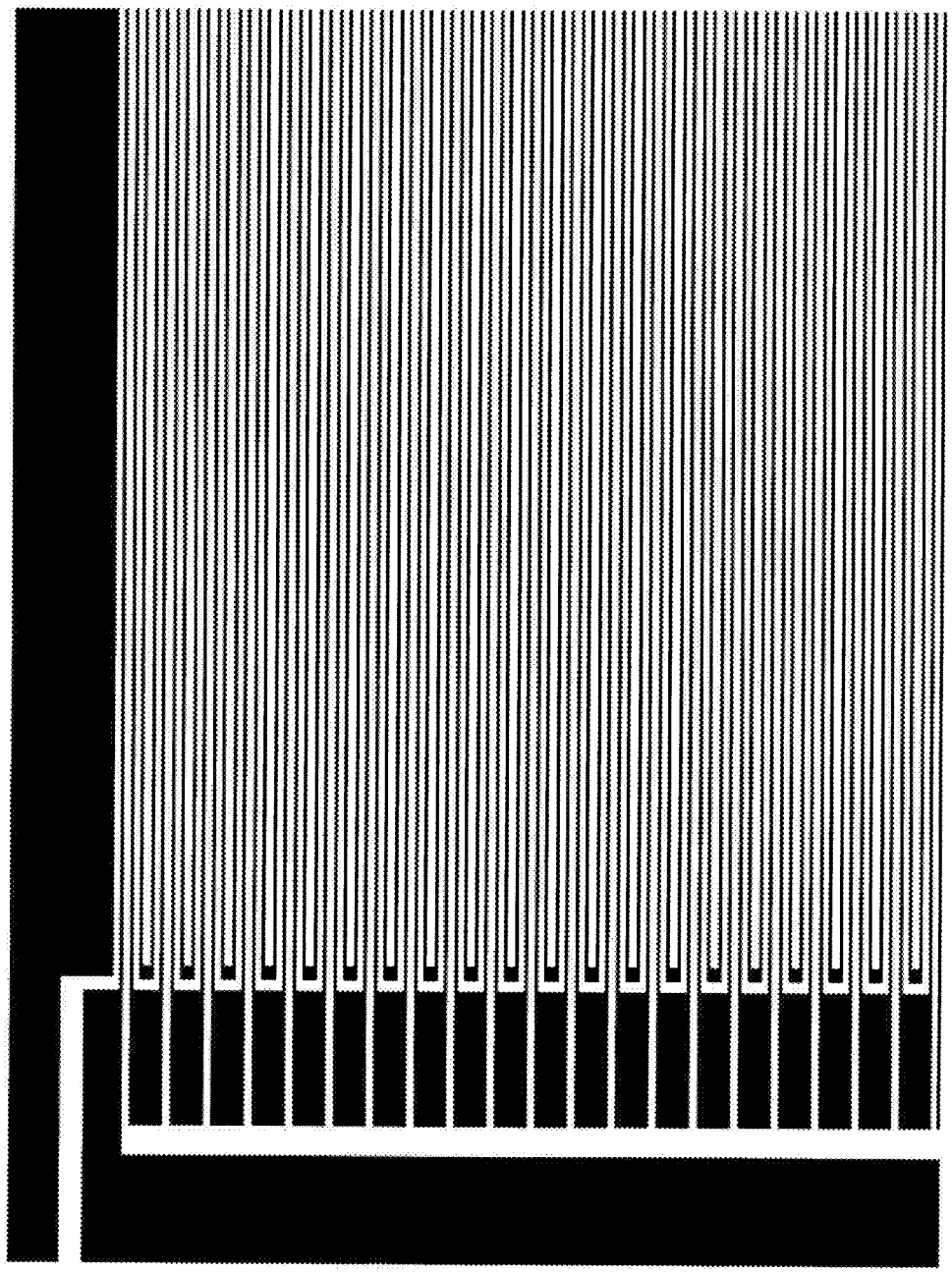
FIG. 7 shows a three-dimensional electrode fabricated using photolithographic patterning of SU-8 (epoxy-based photoresist) on FR-4 printed wiring boards covered with thick copper laminates.

FIG. 7 shows a three-dimensional array fabricated using photolithographic patterning of SU-8 (epoxy-based photoresist, MicroChem, Newton, Mass.) on FR-4 boards covered with thick copper laminates. The laminate thickness provided the height of the three-dimensional electrodes. Typically, the height may reach several hundred microns. The line resolution was 50-70 microns.

The fabrication process utilized the following steps: (i) epoxy was coated with copper at a thickness of between about 50-150 microns thick and was covered with photoresist; (ii) a simple mylar-based mask was made using high resolution laser printing (3600 dpi); (iii) the photoresist was developed with a plastic UV mask and the remaining photoresist was used to protect the unexposed copper regions; (iv) the copper coating was etched in an agitated iron chloride bath for 10-15 minutes to form the three-dimensional electrode array patterns.

Dielectrophoretic separation experiments were performed using polystyrene model particles; other experiments were performed with blood cells spiked with killed E. coli bacteria. Although the dielectrophoretic separation was efficiently visualized under a confocal microscope, discriminating bacterial separation from the blood cells was difficult to observe due to the opaque surface. Several labeling dyes were tested to selectively stain either the blood cells or the bacteria in an effort to improve visualization and quantitation. However, none of the stains were able to increase contrast sufficiently at low dye concentrations without interfering with the dielectrophoretic forces.

Figure 8A:
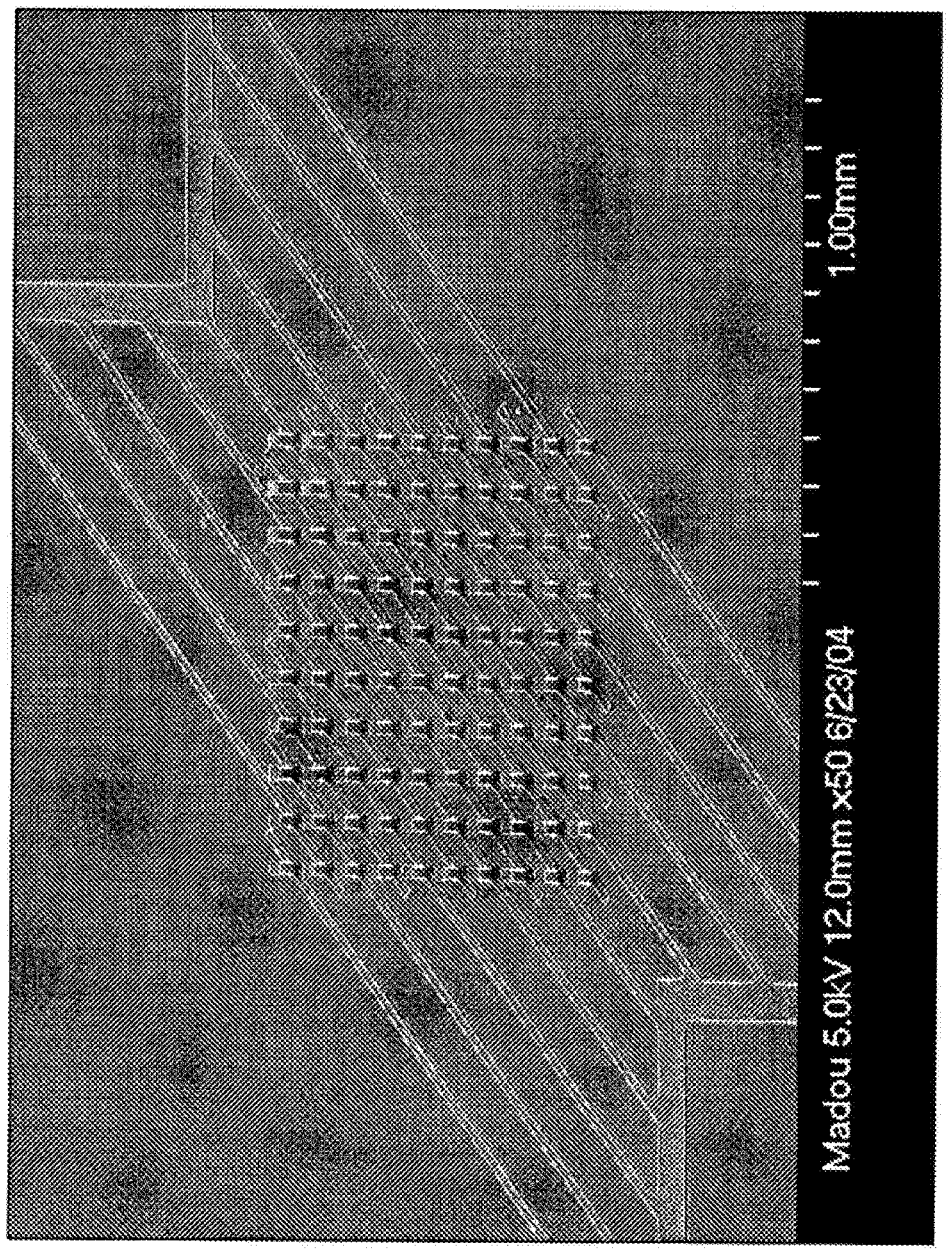
FIGS. 8A, 8B and 8C show three-dimensional electrode arrays fabricated using pyrolized carbon technology in which a photoresist is lithographically patterned and pyrolized under appropriate conditions.
Figure 8B:
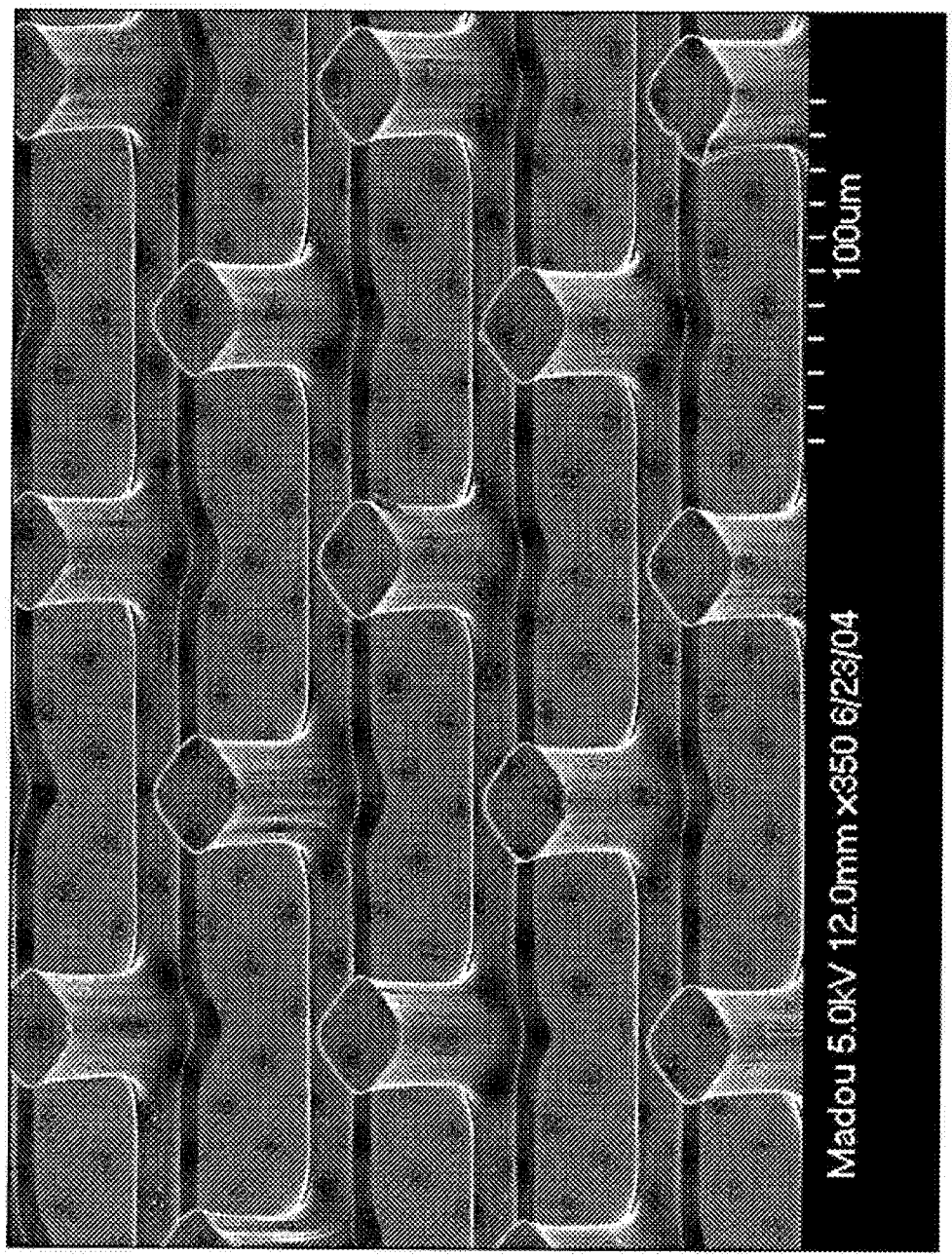
Figure 8C:
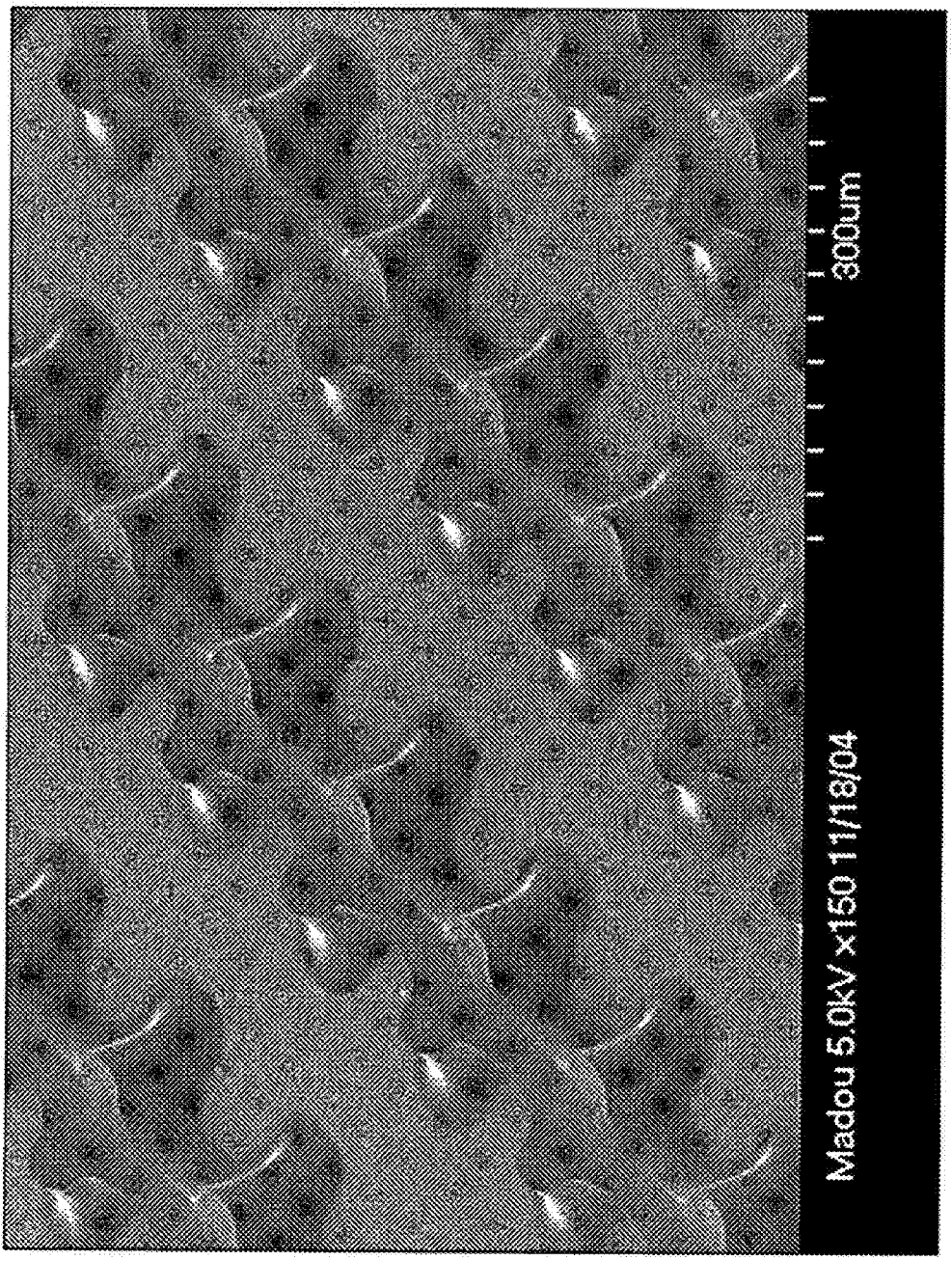

FIG. 8 shows an example of a pyrolized carbon electrode array. In this process, masks were designed using Macromedia Freehand® and printed out on a high resolution printer onto a transparency at 20 times the desired size. The transparencies were projected onto high resolution emulsion masks in a 20:1 reduction camera system, and the masks were developed to generate glass emulsion masks.

As an interconnect layer, the first layer of SU-8 photoresist was spun onto a $SiO_2$ (5000 Å)-coated Si wafer using a two-step spinning process. A first layer of 25 μm was generated using SU-8 and spinning at 500 rpm for 12 seconds, followed by a spin of 2000 rpm for 30 seconds. The wafer was then baked for 3 minutes at 65° C. and then 10 minutes at 95° C. to prevent excessive stress from building up inside the SU-8 layer. The SU-8 photoresist was then exposed to UV light through a mask at 200 mJ/cm². The wafer was then baked for 1 minute at 65° C. and then 3 minutes at 95° C. to allow the photoresist to crosslink.

Development can be carried out after the application of each layer. Alternatively, the development can be completed after all layers are applied and exposed. The SU-8 was developed by immersing the SU-8 developer solution until all unexposed SU-8 is removed.

Posts were generated by repeating application of the SU-8 photoresist, baking, exposure to UV light and post-exposure baking. For example, to generate posts 100 μm thick, the soft bake time was 10 minutes at 65° C. and 40 minutes at 95° C. The samples were then aligned and exposed to masks using the Quintel aligner with a dosage of 400 mJ/cm². The post-exposure bake times were 1 minute at 65° C. and 10 minutes at 95° C.

The multi-layered SU-8 samples were carbonized in an open-ended furnace under an inert atmosphere. First, the samples were post-baked at 300° C. for 30 minutes and then ramped up to 900° C. under a $N_2$ atmosphere. The samples were subsequently held at 900° C. for 60 minutes under forming gas (95% $N_2$/5% $H_2$). The samples were cooled in a $N_2$ atmosphere to room temperature. The $N_2$ and forming gases flowed at 2000 standard cubic centimeters (SCCM) during and after pyrolysis. The heating rate was about 10° C./min and the total cooling time was about 9 hours.

Several array designs were fabricated and tested, including pillar-type electrodes, straight line electrodes, interdigitated electrodes and arrays having varying spacing arrangements between the electrodes and various geometric shapes of electrodes.

Figure 9A:
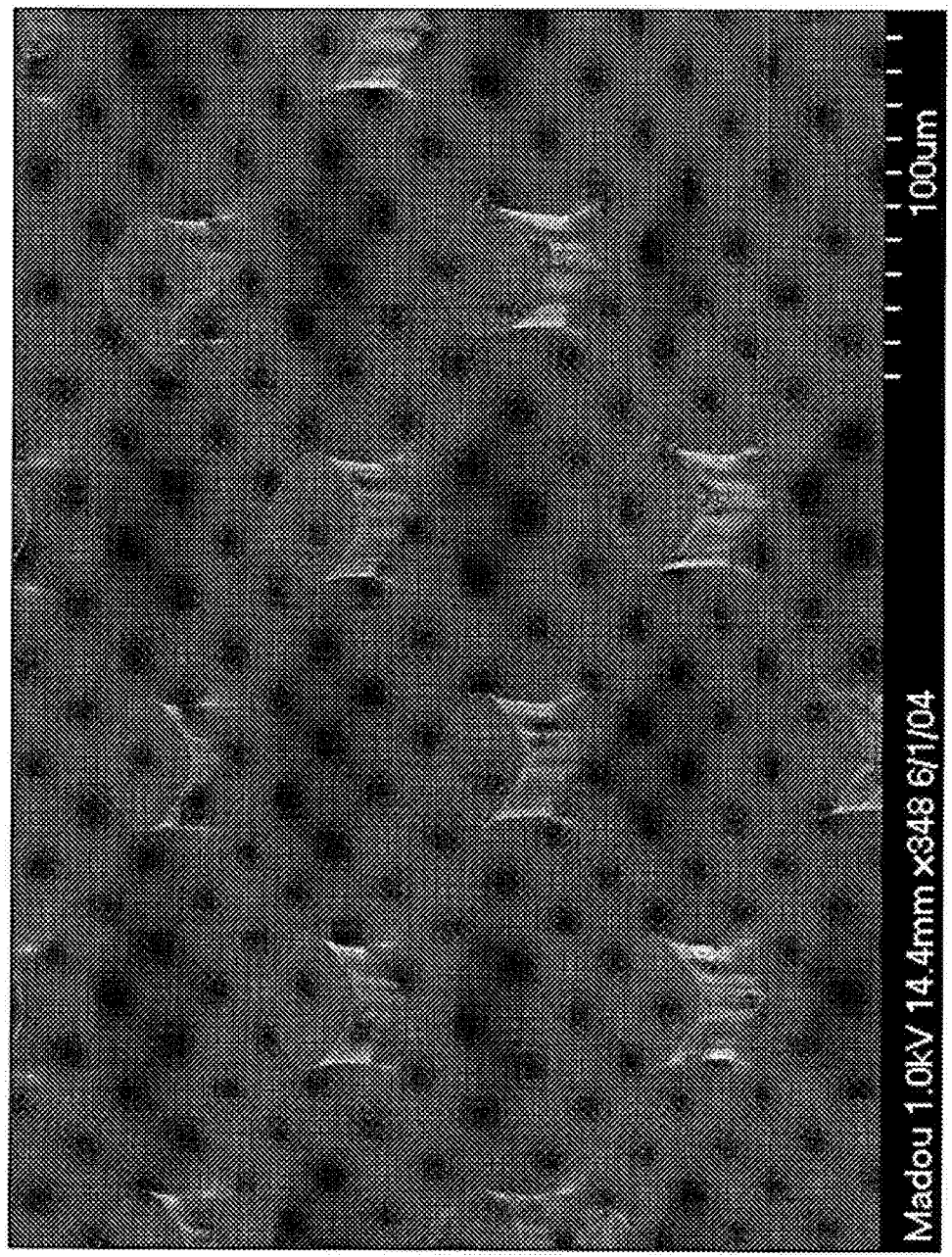
FIGS. 9A and 9B show the secondary pyrolization of a photoresist layer having a conductivity lower than the pillar electrodes.
Figure 9B:
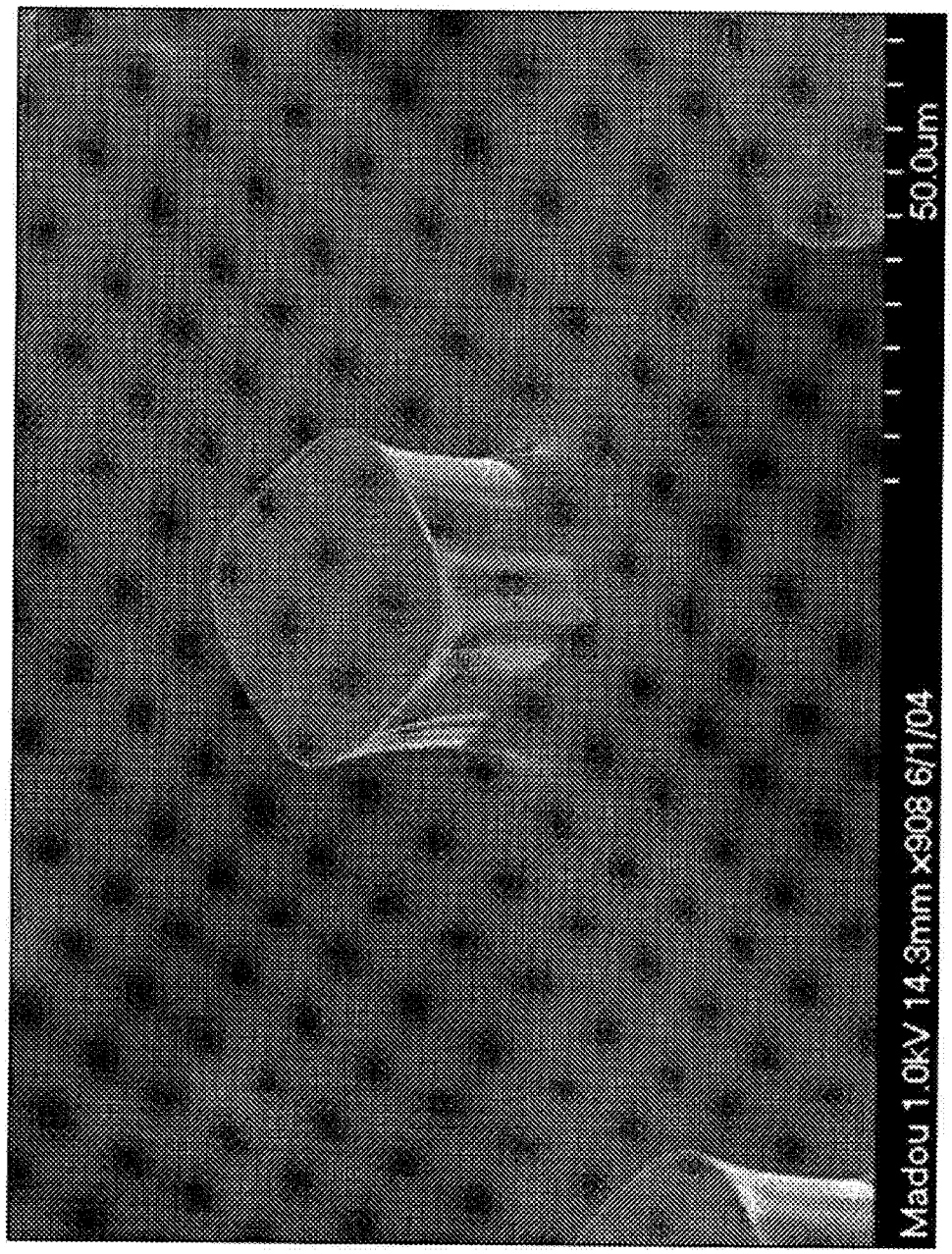

FIG. 9 shows an electrode array fabricated using two layers of pyrolyzed photoresist templated through different masks. A lower conductivity photoresist layer was deposited between the electrode pillars such that the only the pillar electrodes were conductive and exposed to sample solution. Experiments with polystyrene particles demonstrated that screening of the contact wires between the pillar electrodes was unnecessary because the electric field and DEP forces were strong enough on the pillar electrodes for efficient separation. Three-dimensional electrode arrays extending to 1×1 cm were fabricated using this method.

Figure 10:
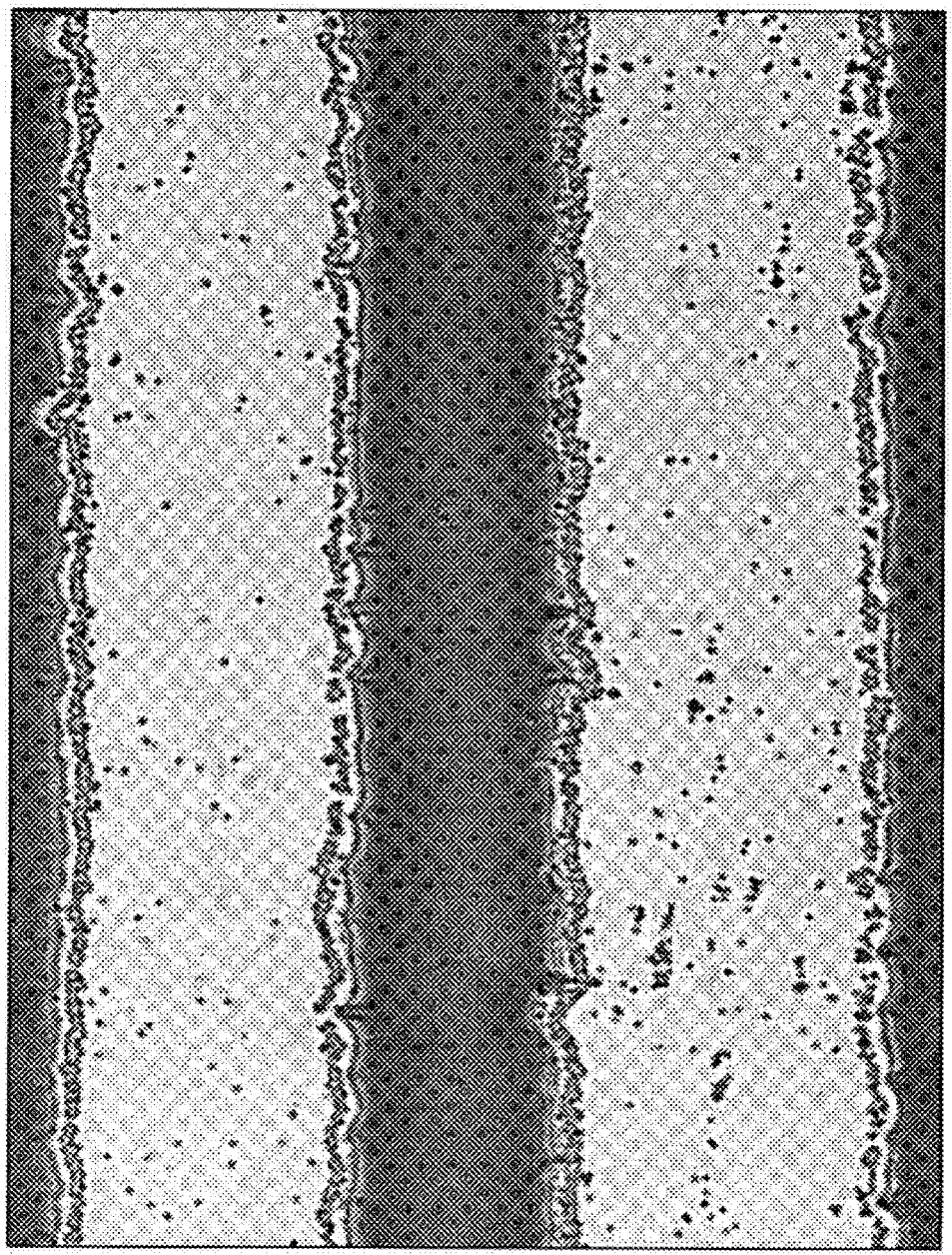
FIG. 10 shows three-dimensional separation of polystyrene model particles, which have a diameter of 5 microns.
Figure 11A:
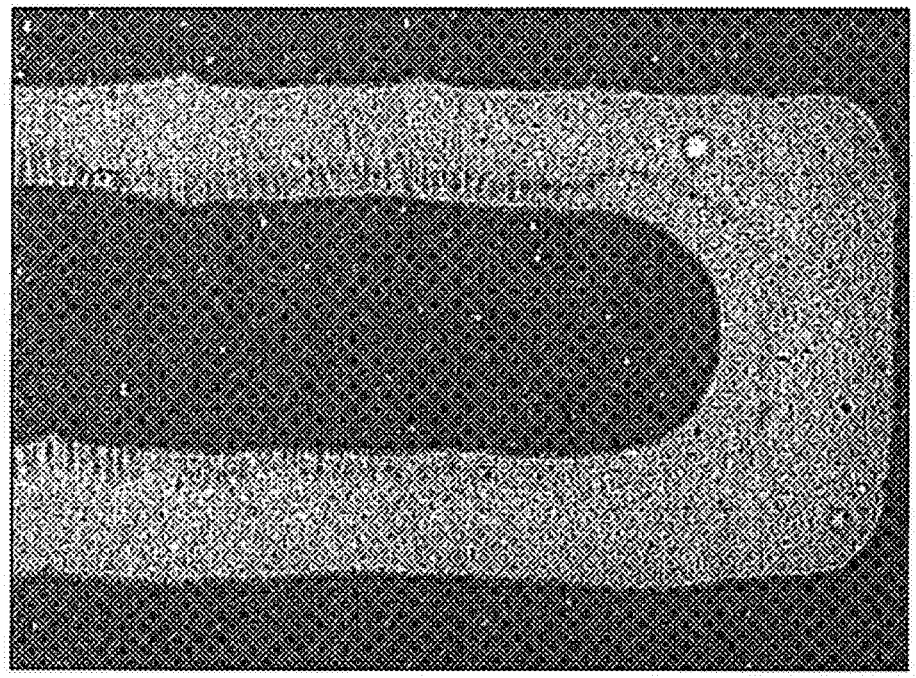
FIG. 11A is 0 minutes.
Figure 11B:
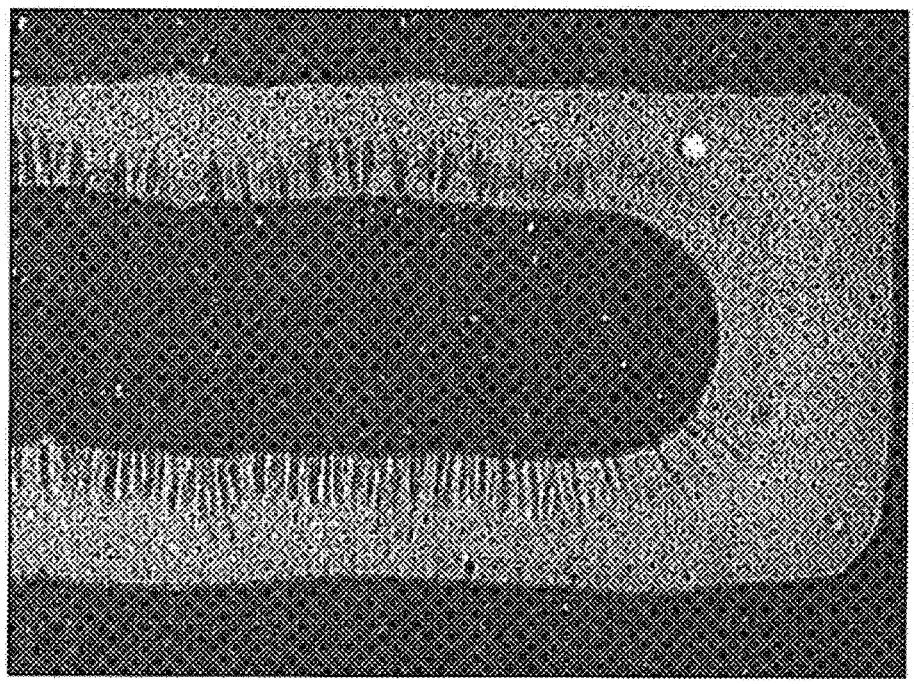
FIG. 11B is 1 minute.
Figure 11C:
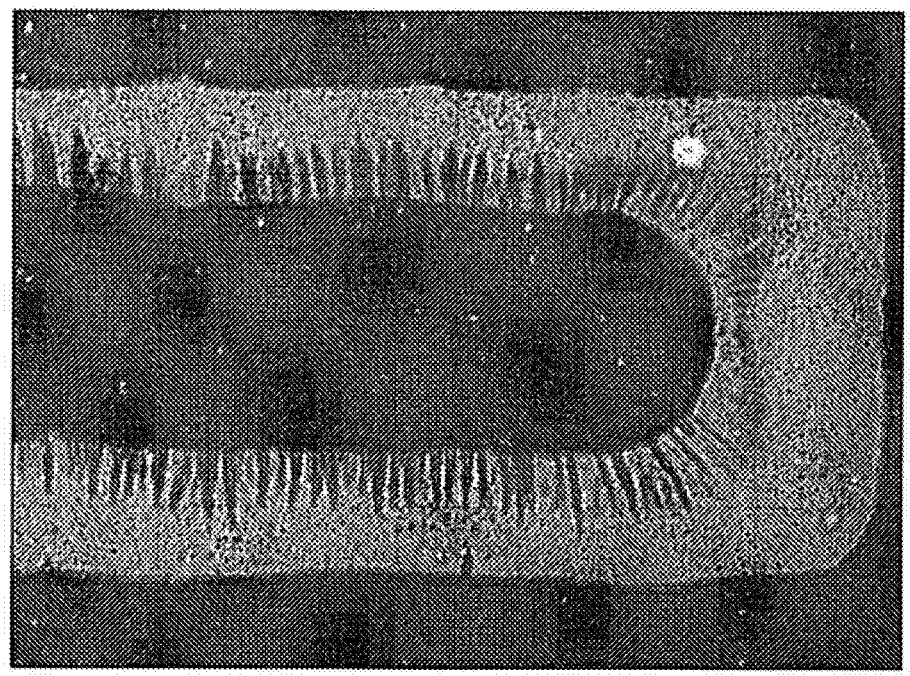
FIG. 11C is 2 minutes.
Figure 11D:
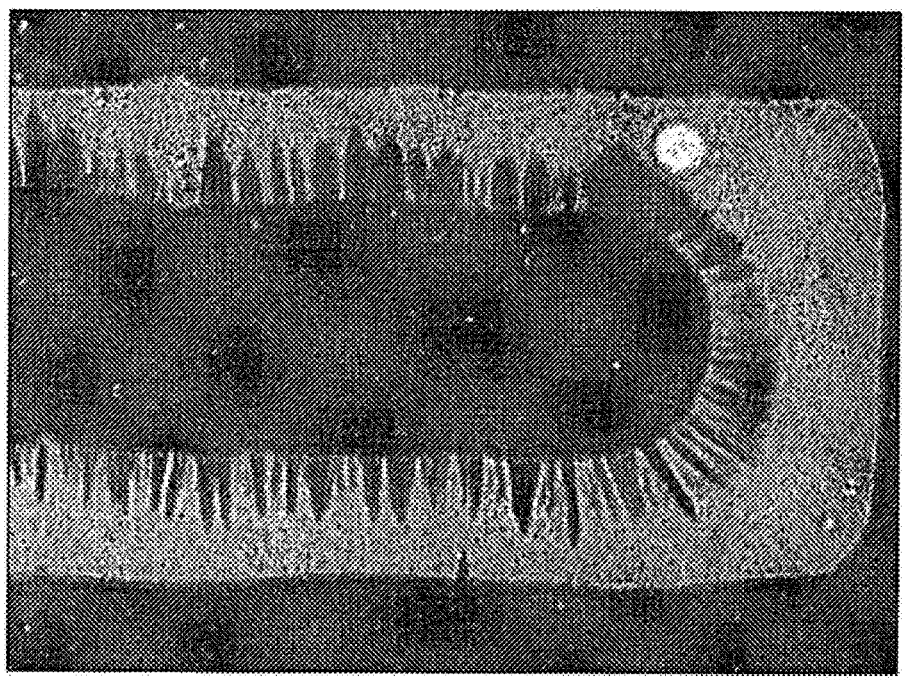
Figure 11E:
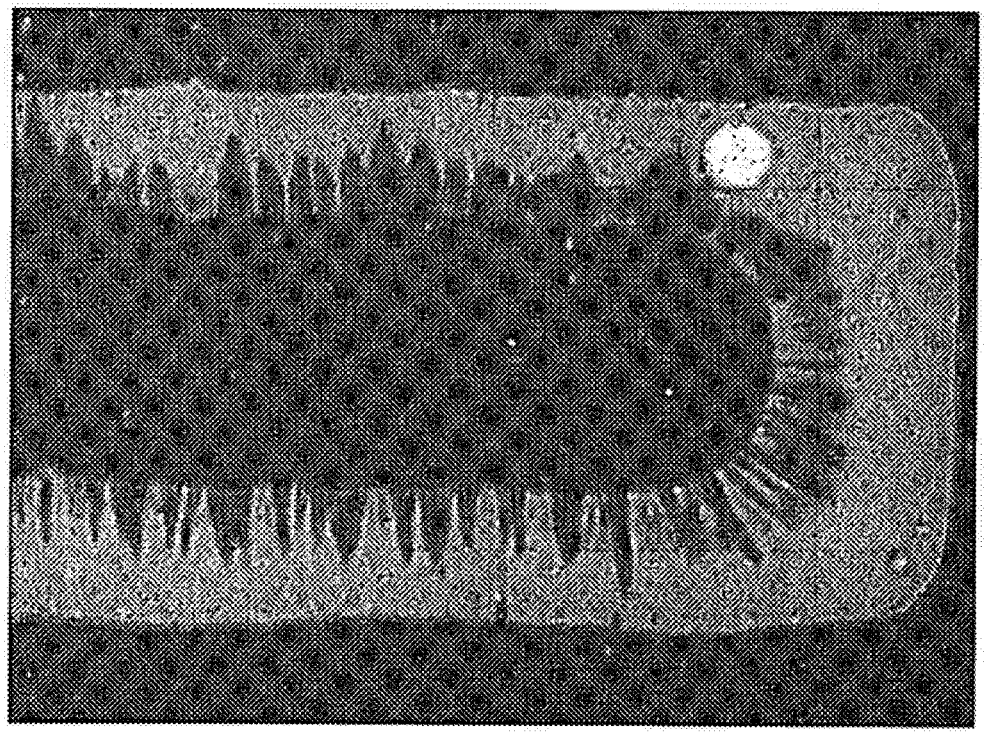
FIG. 11E is 4 minutes. The AC frequency was 110 kHz with an AC field amplitude of 20V.
Figure 12A:
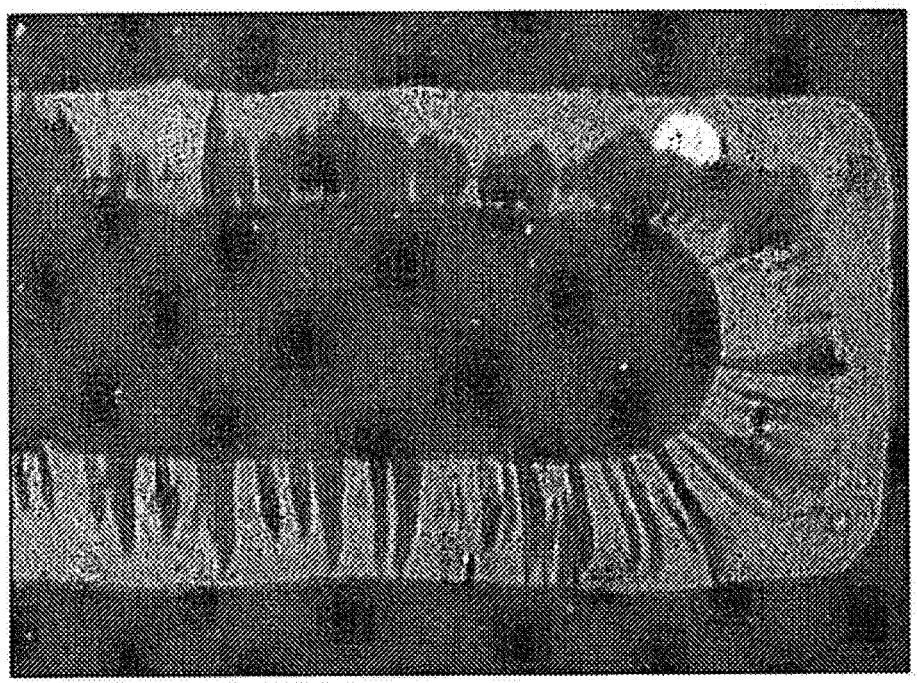
FIG. 12A is separation with an AC field amplitude of 20V.
Figure 12B:
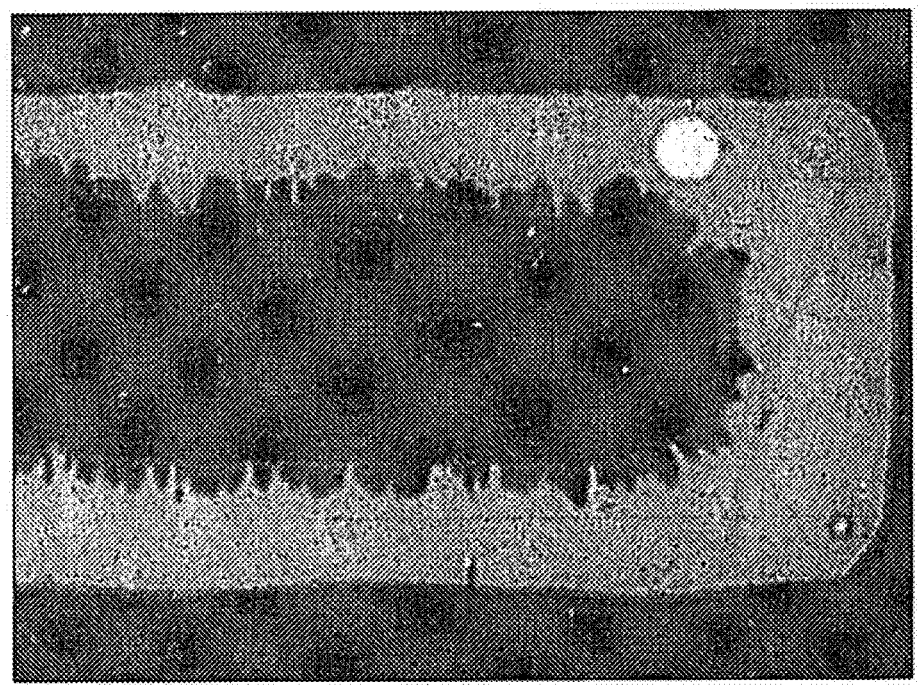
FIG. 12B is separation with an AC field amplitude of 10 V.

FIG. 10 shows an efficient separation of model polystyrene particles using a pyrolized linear electrode array, with model particles varying in size from 1.5-90 microns in diameter. Using this technique, electrode heights as high as about 300 microns and a deposition resolution between electrodes of about 50 microns can be obtained.

Another method of array fabrication utilizes screen printing of carbon on polymer sheet materials. The screen printing was performed using the services of Conductive Technologies, Inc. Electrodes were screen printed using pastes having thicknesses ranging from between about 50-150 microns, which could be printed in multiple layers to allow fabrication of high electrodes and to enable processing larger volumes of biological sample within the flow chamber. Screen printed carbon electrodes, with the addition of a modified electrolyte (described below), allowed voltages up to about 30V, thereby enabling fast and efficient DEP separation.

Optimization of Conditions for 3D Dielectrophoretic Separation

Efficient DEP separation requires consideration of the electrolyte conductivity of the biological sample, the dielectric properties of the electrolyte and analyte, the geometric shape of the electrode array, and the characteristics of the electric field to be applied to the biological sample.

Initially, biological samples of blood were diluted in PBS, which functioned to prevent blood cell coagulation. However, the relatively high conductivity of PBS, approaching mS/cm, prohibited efficient dielectrophoretic separation. Adding mannitol to the PBS solution maintained the integrity of the blood cells in the sample, but the conductivity achieved was too high for efficient DEP separation. Moreover, with the PBS/mannitol solution, during superimposed DC voltage (>2V) or at low frequencies AC (<4 kHz) biasing, bubbles formed in the solution, which prohibited long term and efficient separation.

Addition of α-thioglycerol to the electrolyte solution reduces oxygen evolution and bubbling during separations requiring high voltages. At lower voltages, the α-thioglycerol oxidizes and generates hydrogen ions that function as electrical charge carriers in the electrolyte solution. Moreover, substitution of α-thioglycerol for 0.1% PBS in a PBS/mannitol solution reduced the conductivity of the electrolyte solution to around 55 µS/cm. This lower conductivity enhanced the dielectrophoretic separation and minimized bubble formation during DC biasing at −3.75V. Electrolyte solutions containing 125 mM α-thioglycerol also minimizes cell adhesion and clumping in biological samples.

Figure 16A:
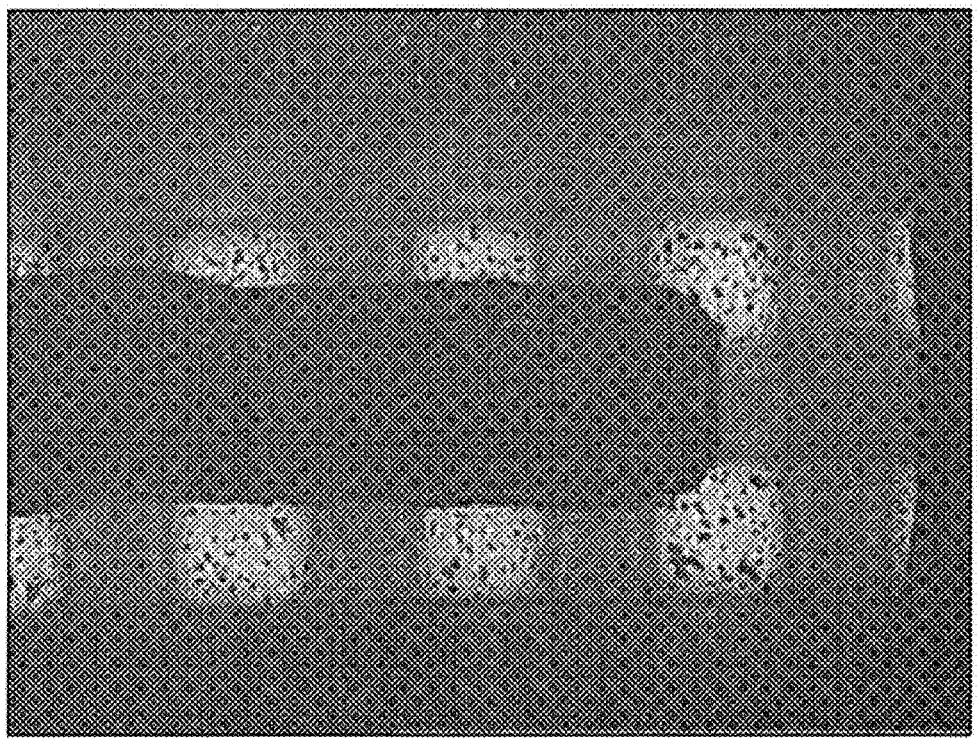
Figure 16B:
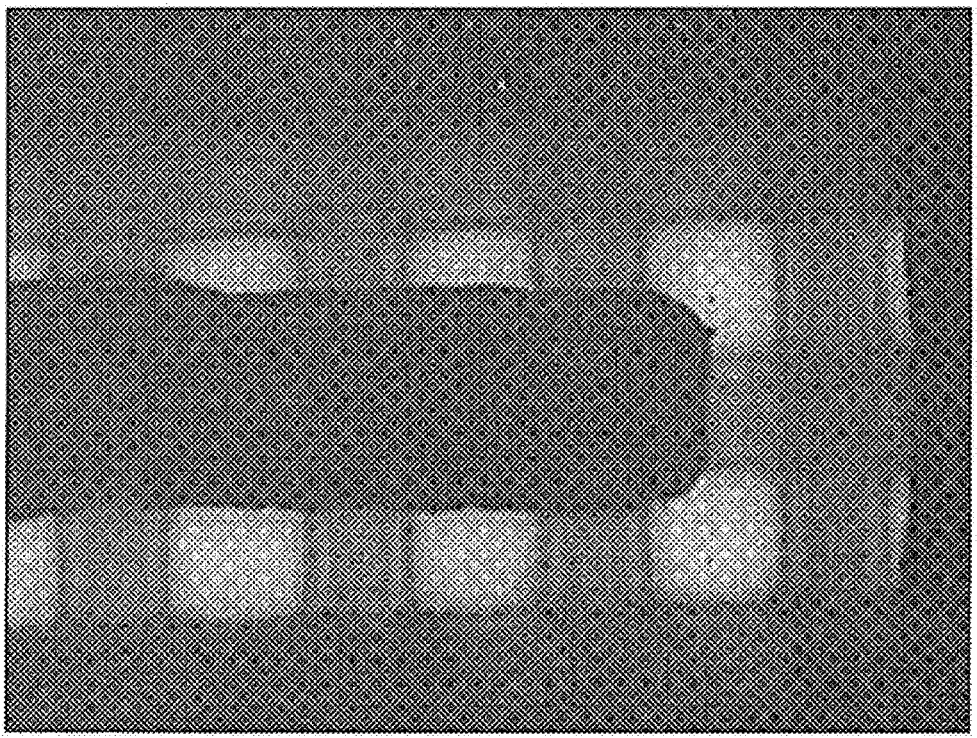

FIG. 16 depicts 3D DEP separation on 100 micron-thick carbon screen printed electrodes. The AC field amplitude (1-48V) and frequency range (DC, 1 Hz-150 kHz) were optimized for speed of DEP separation by real-time monitoring of the process under a confocal microscope. The power supply described above allowed application of high fields at high frequencies and achieved efficient separation at 110 kHz and between about 15-20V within seconds. FIG. 17 shows a time-course of 3D DEP separation at the optimized frequency of 110 kHz. The shape of microparticle accumulation depend on the separation parameters. For example, if the AC amplitude was changed while maintaining the same frequency (e.g., 110 kHz), the particles moved in the opposite direction from the accumulating cells. As shown in FIG. 17, by using the appropriate electrolyte, AC voltages as high as 30V could be used with screen printed carbon electrodes. These results demonstrate that much more efficient DEP separations under these conditions can be achieved as compared to DEP separations typically conducted using voltages between 5-10V.

Figure 13:
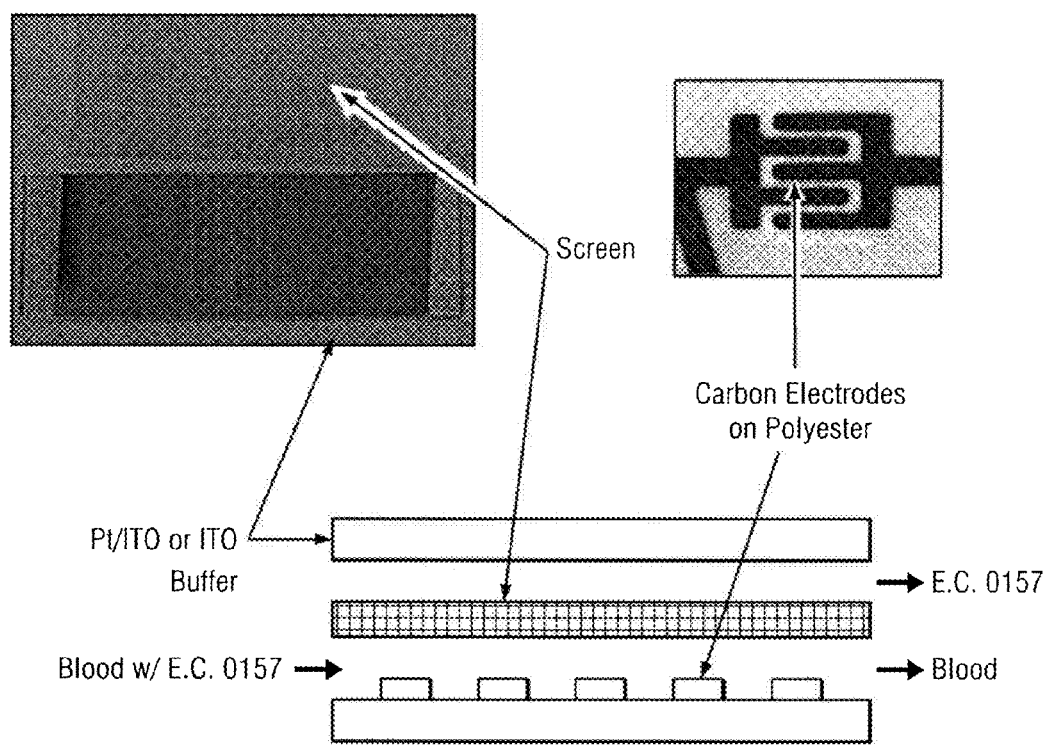
FIG. 13 is a schematic of the three-dimensional dielectrophoretic separator of the present invention.

FIG. 13 shows an optimized design of a two compartment, three dimensional dielectrophoretic separator of the present invention. According to this embodiment, a mesh plastic separator was used between the two chambers. The contact to the electrodes was established using micropositioners.

Figure 14D:
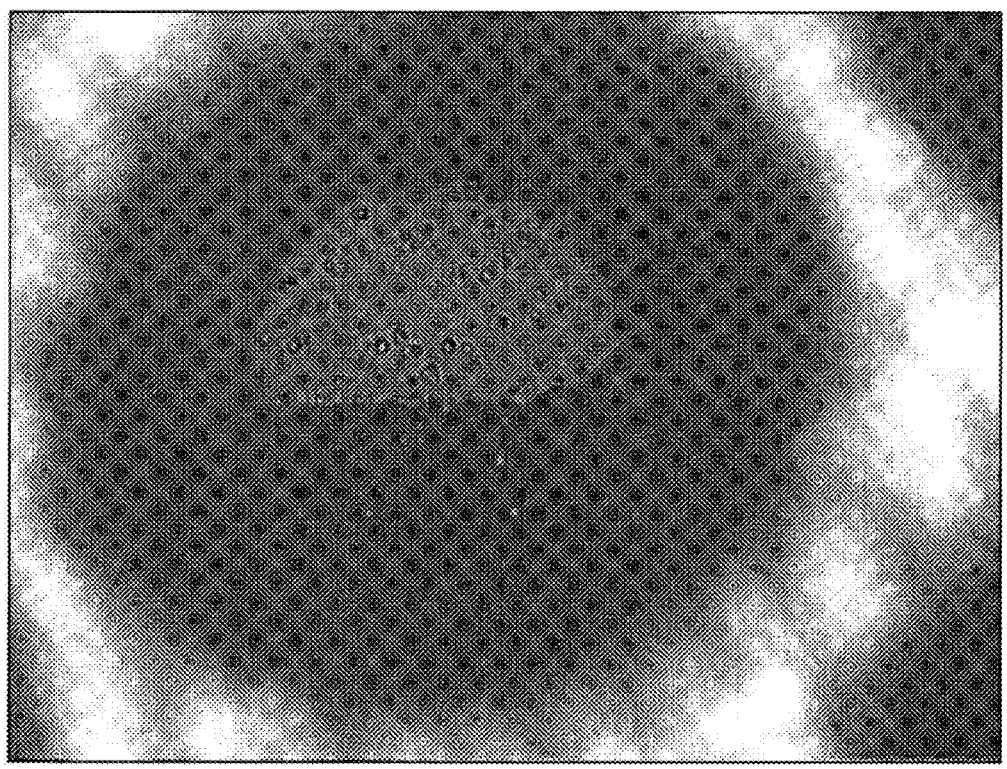
FIG. 14 illustrates two types of separators that may be used between the DEP separation and collection compartments—a mesh separator is shown in FIG. 14A, a plastic separator is shown in FIG. 14B, and separators containing geometrical openings are shown in FIGS. 14C and 14D.

In other embodiments, other types of separators were utilized. In particular, mesh net plastic separators can be used, as well as plastic separators configured with openings assuming various geometric shapes and sizes depending on the particular properties of the particles to be collected in the upper chamber. Those of ordinary skill in the art are adept at selecting a particular geometrical shape for inclusion in the invention. Such shapes include, but are not limited to circles, squares, triangles, rectangles, parallelograms, rhombus, trapezoids, ellipses, polygons, and the like with varying dimensions capable of serving as and providing size exclusion mechanisms. For example, the geometrical shapes may be formed in a variety of different sizes depending on the particular sample chosen to be separated. Moreover, the separator may be configured with a combination of geometrical shapes. FIG. 14 shows the optical image seen through the top transparent indium tin oxide electrode and focused in the upper electrophoretic collection chamber. FIG. 14 shows bacteria that were separated in the lower chamber (as viewed through the separator).

The E. coli Test

Figure 15A:
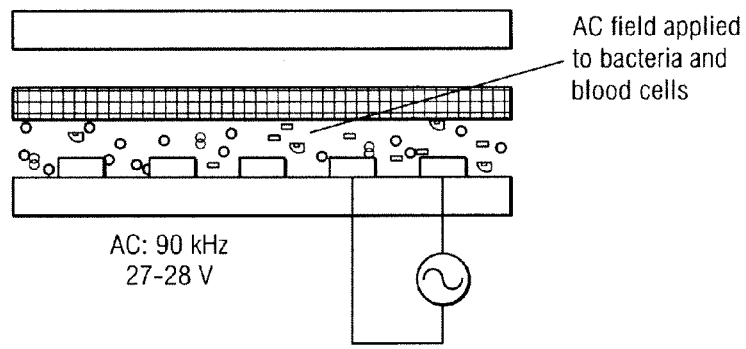
FIG. 15 is a schematic diagram illustrating a process for separating E. coli from blood cells in a blood sample using the three-dimensional dielectrophoretic separator of the present invention.
Figure 15B:
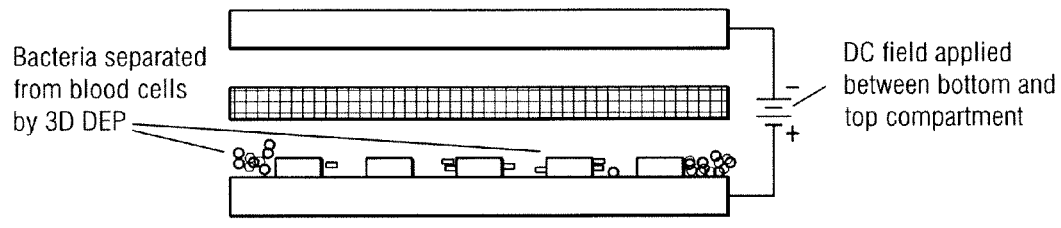
Figure 15C:
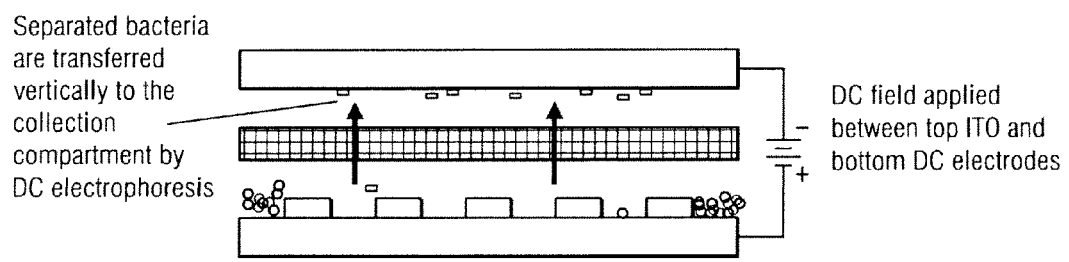

FIG. 15 illustrates the process used to separate E. coli O157 spiked into a sample of human blood cells. Samples were prepared in dilutions up to 1:20 and mixed with an electrolyte solution of 125 mM α-thioglycerol in 280 mM mannitol, which minimizes bubbling and cell clumping. The samples were separated in a flow chamber having an array of interdigitated screen printed carbon electrodes using voltages up to 30V.

FIG. 16 depicts the separation process. The interdigitated electrodes facilitated movement of the blood cells away from the edges of the electrode array. A DC electrophoretic field was then applied to the sample and the bacteria in the sample moved vertically to the upper chamber.

The efficiency of three dimensional DEP and electrophoretic separation of bacteria and blood cells in a blood sample was determined by counting the number of blood cells and bacteria in the sample pre- and post-separation using the Petrof-Hauser counting method. A sample of bacteria from the upper chamber was extracted using a small calibrated capillary. Appropriate dilutions and repeated counting (n=3) were performed for each sample. The average percentage of cells present in the bacteria sample after separation was determined. Prior to separation, the sample contained 60% E. coli O157 (17.0±1.0, n=3) and 40% blood cells (11.5±3.1, n=3). After separation, the upper chamber contained 100% E. coli O157 (6.7±0.6, n=3) and 0% blood cells (0.0±0.0, n=3). Repeated experiments and optimization of 3D DEP and electrophoretic conditions yielded high separation efficiency for the apparatus of the present invention. In all the experiments, the "purity" of bacteria in the upper chamber was near 100%.

In a flow cell containing a single array of interdigitated electrodes, the typical sample size was between about 15-20 µl, which volume represents a four-fold increase in volume as compared to previously used two-dimensional systems. Expanding the size of the electrode array to approximately 10 cm wide will enable the use of a larger flow chamber capable of processing a sample between about 1-2 ml. Larger sample volumes have the added benefit of ensuring higher sensitivity in the detection methods.

Additional Designs

In order to process larger biological sample sizes, a "wrapped" 3D DEP separator was developed by sputtering metal on a polyester sheet. More specifically, platinum was sputtered at a thickness of about 100 nm, although other metals may be employed in this process with equal effectiveness. The metallized sheet was then inserted in a high resolution inkjet printer, and a computer-generated pattern was printed directly on the metallized sheet. The printer wax provided an insulating zone between the electrodes. FIG. 23 depicts two geometries of "wrapped" 3D electrode arrays.

A "wrappable" ink jet printed 3D DEP electrode array may be assembled with plastic separators between the electrode arrays. One electrode could be a non-patterned metallic sheet while the other electrode could be patterned as shown in FIG.

23. This type of electrode arrangement will allow high non-uniformity of the electric fields and efficient separation.

While certain embodiments of the present invention have been shown and described in detail, it will be readily apparent to those skilled in the art, in light of these teachings, that certain changes and modifications may be made thereto without departing from the spirit or scope of the appended claims.

We claim:

1. An apparatus for separating particles within a biological sample by dielectrophoresis, the apparatus comprising:
   a flow chamber for accepting the biological sample, the flow chamber having an upper chamber and a lower chamber;
   a separator disposed between the upper chamber and the lower chamber;
   a first electrode array disposed in the flow chamber, the first electrode array comprising a plurality of vertical and horizontal electrodes, wherein the plurality of vertical electrodes are in electrical communication with an AC power source and wherein the plurality of horizontal electrodes are in electrical communication with a DC power source.

2. The apparatus of claim 1, wherein the plurality of vertical electrodes are arranged in an interdigitated configuration.

3. The apparatus of claim 1, wherein the separator is fabricated of mesh netting.

4. The apparatus of claim 1, wherein the separator is fabricated of plastic having geometrical openings.

5. The apparatus of claim 4, wherein the geometrical openings are selected from the group of circles, squares, triangles, rectangles, parallelograms, rhombus, trapezoids, ellipses, polygons and any combination thereof.

6. The apparatus of claim 1, wherein the flow chamber has an approximate volume of about 10 microliters.

7. The apparatus of claim 1, wherein the flow chamber has an approximate volume of about 5 milliliters.

8. The apparatus of claim 1, wherein the plurality of horizontal electrodes are in electrical communication with an AC power source.

9. A method of manipulating biological samples comprising a mixture of desired cellular materials and undesired cellular materials, the manipulation being carried out in a dielectrophoretic system including a flow chamber including an upper chamber, a lower chamber and an array of electrodes, the method comprising the steps of:
   introducing a biological sample into the flow chamber of the system;
   subjecting the biological sample to a dielectrophoretic force in the lower chamber such that the desired cells collect in the lower chamber and the undesired cells collect in the upper chamber, wherein an AC field amplitude ranging from between about 1 V to about 48 V is applied to a plurality of vertically arranged electrodes disposed in the flow chamber and wherein a DC frequency ranging from between about 1 Hz to about 150 kHz is applied to a plurality of horizontally arranged electrodes disposed in the flow chamber.

10. The method of claim 9, further comprising the step of treating the biological sample with an immunological reagent prior to introducing the biological sample into the flow chamber.

11. The method of claim 9, further comprising the step of introducing an immunological reagent to the flow chamber after introducing the biological sample into the flow chamber.

* * * * *